(12) United States Patent
Bar-Yoseph et al.

(10) Patent No.: US 8,725,249 B2
(45) Date of Patent: May 13, 2014

(54) STIMULATION OF THE URINARY SYSTEM

(75) Inventors: Gill Bar-Yoseph, Haifa (IL); Aviv Levi, Natanya (IL); David Bleicher, Tel Aviv-Yafo (IL); Alon Polsky, Misgav (IL)

(73) Assignee: Nephera Ltd., Caesarea (IL)

( * ) Notice: Subject to any disclaimer, the term of this patent is extended or adjusted under 35 U.S.C. 154(b) by 100 days.

(21) Appl. No.: 13/415,594

(22) Filed: Mar. 8, 2012

(65) Prior Publication Data

US 2012/0226098 A1 Sep. 6, 2012

Related U.S. Application Data

(63) Continuation-in-part of application No. 13/156,753, filed on Jun. 9, 2011, which is a continuation-in-part of application No. PCT/IL2009/001163, filed on Dec. 9, 2009.

(60) Provisional application No. 61/120,901, filed on Dec. 9, 2008, provisional application No. 61/173,228, filed on Apr. 28, 2009, provisional application No. 61/180,957, filed on May 26, 2009, provisional application No. 61/218,139, filed on Jun. 18, 2009, provisional application No. 61/225,226, filed on Jul. 14, 2009, provisional application No. 61/233,500, filed on Aug. 13, 2009, provisional application No. 61/355,522, filed on Jun. 16, 2010, provisional application No. 61/451,406, filed on Mar. 10, 2011.

(51) Int. Cl.
*A61N 1/00* (2006.01)

(52) U.S. Cl.
USPC .............................. 607/3; 607/40; 623/23.65

(58) Field of Classification Search
USPC ............... 607/40; 600/29; 606/41; 623/23.65
See application file for complete search history.

(56) References Cited

U.S. PATENT DOCUMENTS

| 4,850,963 | A | * | 7/1989 | Sparks et al. | .................. 600/29 |
|---|---|---|---|---|---|
| 5,374,261 | A | | 12/1994 | Yoon | |
| 5,425,703 | A | | 6/1995 | Feiring | |
| 5,443,470 | A | | 8/1995 | Stern et al. | |
| 5,449,971 | A | | 9/1995 | Scott et al. | |
| 5,505,730 | A | | 4/1996 | Edwards | |

(Continued)

FOREIGN PATENT DOCUMENTS

| CN | 2598571 Y | 1/2004 |
|---|---|---|
| RU | 2271840 | 2/2004 |

(Continued)

OTHER PUBLICATIONS

Office Action dated Apr. 18, 2013 issued during the prosecution of U.S. Appl. No. 13/156,753.

(Continued)

*Primary Examiner* — Christopher D Koharski
*Assistant Examiner* — Michael Carey
(74) *Attorney, Agent, or Firm* — Edwards Wildman Palmer LLP; Barry Kramer; Lisa Swiszcz

(57) ABSTRACT

Apparatus and methods are described including identifying a subject as suffering from an impaired body system, the body system being selected from the group consisting of: a cardiovascular system and a renal system. In response thereto, a structure is inserted inside a bladder of the subject, and the bladder is mechanically stimulated with the structure. Other applications are also described.

33 Claims, 20 Drawing Sheets

(56) References Cited

U.S. PATENT DOCUMENTS

| | | | |
|---|---|---|---|
| 5,531,676 A | 7/1996 | Edwards et al. | |
| 5,536,240 A | 7/1996 | Edwards et al. | |
| 5,588,960 A | 12/1996 | Edwards et al. | |
| 5,704,908 A | 1/1998 | Hofmann et al. | |
| 5,733,319 A | 3/1998 | Neilson et al. | |
| 5,749,845 A | 5/1998 | Hildebrand et al. | |
| 5,769,880 A | 6/1998 | Truckai et al. | |
| 5,840,076 A | 11/1998 | Swanson et al. | |
| 5,861,431 A * | 1/1999 | Hildebrand et al. | 514/557 |
| 6,009,877 A | 1/2000 | Edwards | |
| 6,056,744 A | 5/2000 | Edwards | |
| 6,061,596 A | 5/2000 | Richmond et al. | |
| 6,254,599 B1 | 7/2001 | Lesh et al. | |
| 6,425,877 B1 | 7/2002 | Edwards | |
| 6,500,158 B1 | 12/2002 | Ikeguchi | |
| 6,662,052 B1 | 12/2003 | Sarwal et al. | |
| 6,685,744 B2 | 2/2004 | Gellman et al. | |
| 6,692,490 B1 * | 2/2004 | Edwards | 606/41 |
| 6,699,216 B2 | 3/2004 | Ikeguchi | |
| 6,743,197 B1 | 6/2004 | Edwards | |
| 6,743,226 B2 | 6/2004 | Cosman et al. | |
| 6,978,174 B2 | 12/2005 | Gelfand et al. | |
| 6,990,376 B2 | 1/2006 | Tanagho et al. | |
| 6,994,706 B2 | 2/2006 | Chornenky et al. | |
| 7,162,303 B2 | 1/2007 | Levin et al. | |
| 7,326,235 B2 | 2/2008 | Edwards | |
| 7,433,734 B2 | 10/2008 | King | |
| 7,470,228 B2 | 12/2008 | Connors et al. | |
| 7,617,005 B2 | 11/2009 | Demarais et al. | |
| 7,620,451 B2 | 11/2009 | Demarais et al. | |
| 8,032,222 B2 | 10/2011 | Loushin et al. | |
| 2001/0003798 A1 | 6/2001 | McGovern et al. | |
| 2001/0031941 A1 | 10/2001 | Edwards et al. | |
| 2005/0049475 A1 | 3/2005 | Gregersen | |
| 2005/0143783 A1 | 6/2005 | Boveja et al. | |
| 2005/0228459 A1 | 10/2005 | Levin et al. | |
| 2005/0228460 A1 | 10/2005 | Levin et al. | |
| 2005/0234523 A1 | 10/2005 | Levin et al. | |
| 2005/0288730 A1 | 12/2005 | Deem et al. | |
| 2006/0025821 A1 | 2/2006 | Gelfand et al. | |
| 2006/0041277 A1 | 2/2006 | Deem et al. | |
| 2006/0116720 A1 | 6/2006 | Knoblich | |
| 2006/0142801 A1 | 6/2006 | Demarais et al. | |
| 2006/0206002 A1 * | 9/2006 | Frassica et al. | 600/101 |
| 2006/0206150 A1 | 9/2006 | Demarais et al. | |
| 2006/0212076 A1 | 9/2006 | Demarais et al. | |
| 2006/0212078 A1 | 9/2006 | Demarais et al. | |
| 2006/0235474 A1 | 10/2006 | Demarais | |
| 2006/0265014 A1 | 11/2006 | Demarais et al. | |
| 2006/0265015 A1 | 11/2006 | Demarais et al. | |
| 2006/0271111 A1 | 11/2006 | Demarais et al. | |
| 2006/0276852 A1 | 12/2006 | Demarais et al. | |
| 2007/0066957 A1 | 3/2007 | Demarais et al. | |
| 2007/0083239 A1 | 4/2007 | Demarais et al. | |
| 2007/0112327 A1 | 5/2007 | Yun et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0173899 A1 | 7/2007 | Levin et al. | |
| 2007/0203549 A1 | 8/2007 | Demarais et al. | |
| 2007/0207959 A1 | 9/2007 | Pisegna et al. | |
| 2007/0208382 A1 | 9/2007 | Yun | |
| 2007/0265687 A1 | 11/2007 | Deem et al. | |
| 2007/0282184 A1 | 12/2007 | Roberts | |
| 2008/0065167 A1 | 3/2008 | Boggs et al. | |
| 2008/0119907 A1 | 5/2008 | Stahmann | |
| 2008/0213331 A1 | 9/2008 | Gelfand et al. | |
| 2008/0249439 A1 | 10/2008 | Tracey et al. | |
| 2008/0255642 A1 | 10/2008 | Zarins et al. | |
| 2009/0024195 A1 | 1/2009 | Rezai et al. | |
| 2009/0036948 A1 | 2/2009 | Levin et al. | |
| 2009/0054950 A1 | 2/2009 | Stephens | |
| 2009/0062873 A1 | 3/2009 | Wu et al. | |
| 2009/0076409 A1 | 3/2009 | Wu et al. | |
| 2009/0221939 A1 | 9/2009 | Demarais et al. | |
| 2009/0247817 A1 | 10/2009 | Forsell | |
| 2009/0254144 A1 | 10/2009 | Bhadra et al. | |
| 2009/0264967 A1 | 10/2009 | Giftakis et al. | |
| 2010/0121220 A1 | 5/2010 | Nishtala | |
| 2010/0226098 A1 | 9/2010 | Loibl et al. | |
| 2010/0274310 A1 | 10/2010 | Boggs, II et al. | |
| 2011/0093026 A1 | 4/2011 | Wariar et al. | |
| 2011/0144468 A1 | 6/2011 | Boggs et al. | |
| 2011/0301662 A1 | 12/2011 | Bar-Yoseph et al. | |
| 2013/0178824 A1 | 7/2013 | Buelna | |

FOREIGN PATENT DOCUMENTS

| | | |
|---|---|---|
| WO | WO-97/44088 A1 | 11/1997 |
| WO | WO-03/020124 A2 | 3/2003 |
| WO | WO-2004/075948 A2 | 9/2004 |
| WO | WO-2010/067360 A2 | 6/2010 |
| WO | WO-2012/027734 A1 | 3/2012 |
| WO | WO 2013/134469 | 9/2013 |

OTHER PUBLICATIONS

Examination Report dated Mar. 18, 2013 issued during the prosecution of corresponding Australian Patent Application No. 2009325847.

International Preliminary Report on Patentability dated Jun. 14, 2011, which issued during the prosecution of Applicant's PCT/IL2009/001163.

Bakunts SA, Muradian KM (1977) Effect of electric stimulation on ureteral function. Zh Eksp Klin Med 17:8-15 with English abstract.

Bencsath P, Szenasi G, Asztalos B, Takacs L (1985) Time course of denervation diuresis and natriuresis in the anaesthetized rat. Acta Physiol Hung 66:47-50. Abstract only.

Blair JE, Khan S, Konstam MA, Swedberg K, Zannad F, Burnett JC, Jr., Grinfeld L, Maggioni AP, Udelson JE, Zimmer CA, Ouyang J, Chen CF, Gheorghiade M (2009) Weight changes after hospitalization for worsening heart failure and subsequent re-hospitalization and mortality in the EVEREST trial. Eur Heart J 30:1666-1673.

Caterina MJ, Schumacher MA, Tominaga M, Rosen TA, Levine JD, Julius D (1997) The capsaicin receptor: a heat-activated ion channel in the pain pathway. Nature 389:816-824.

Chen SS, Chen WC, Hayakawa S, Li PC, Chien CT (2009) Acute urinary bladder distension triggers ICAM-1-mediated renal oxidative injury via the norepinephrine-renin-angiotensin II system in rats. J Formos Med Assoc 108:627-635.

Chien CT, Yu HJ, Cheng YJ, Wu MS, Chen CF, Hsu SM (2000) Reduction in renal haemodynamics by exaggerated vesicovascular reflex in rats with acute urinary retention. J Physiol 526 Pt 2:397-408.

Chuang YC, Fraser MO, Yu Y, Beckel JM, Seki S, Nakanishi Y, Yokoyama H, Chancellor MB, Yoshimura N, de Groat WC (2001) Analysis of the afferent limb of the vesicovascular reflex using neurotoxins, resiniferatoxin and capsaicin. Am J Physiol Regul Integr Comp Physiol 281:R1302-1310.

De Bock F, De Wachter S, Wyndaele JJ (2009) Can the use of different parameters and waveforms improve the results of intravesical electrical stimulation: a pilot study in the rat. Neurourol Urodyn 28:246-250.

Deng PY, Li YJ (2005) Calcitonin gene-related peptide and hypertension. Peptides 26:1676-1685.

Derzhavin VM, Vishnevskii EL, Dzheribal'di OA, Bruk SD, Vasil'ev AI (1989) Electric stimulation of the ureterovesical anastomosis in the treatment of hyperreflexia of the urinary bladder. Pediatriia: 53-57.

DiBona GF (2004) The sympathetic nervous system and hypertension: recent developments. Hypertension 43:147-150.

DiBona GF, Kopp UC (1997) Neural control of renal function. Physiol Rev 77:75-197.

DiBona GF, Sawin LL (1999) Renal hemodynamic effects of activation of specific renal sympathetic nerve fiber groups. Am J Physiol 276:R539-549.

Dwyer TM, Schmidt-Nielsen B (2003) The renal pelvis: machinery that concentrates urine in the papilla. News Physiol Sci 18:1-6.

(56) References Cited

OTHER PUBLICATIONS

Fagius J, Karhuvaara S (1989) Sympathetic activity and blood pressure increases with bladder distension in humans. Hypertension 14:511-517.

Gardiner SM, Compton AM, Kemp PA, Bennett T, Foulkes R, Hughes B (1991) Regional haemodynamic effects of prolonged infusions of human alpha-calcitonin gene-related peptide in conscious, Long Evans rats. Br J Pharmacol 103:1509-1514.

Gotloib L, Fudin R, Yakubovich M, Vienken J (2005) Peritoneal dialysis in refractory end-stage congestive heart failure: a challenge facing a no-win situation. Nephrol Dial Transplant 20 Suppl 7:vii32-36.

Jiang CH, Lindstrom S (1999) Prolonged enhancement of the micturition reflex in the cat by repetitive stimulation of bladder afferents. J Physiol 517 ( Pt 2):599-605.

Kazarian K.V., V. Vanstain et al. Activation of latent pacemakers in the guinea pig ureter. Ross Fiziol Zhlm M. Sechenova 87(7): 953-9, 2001. Abstract Only.

Kenton K, Simmons J, FitzGerald MP, Lowenstein L, Brubaker L (2007) Urethral and bladder current perception thresholds: normative data in women. J Urol 178:189-192; discussion 192.

Kolesnikow GP, Karpenko WS (1987) Development and assessment of an artificial pacemaker of the ureter with feedback. Z Urol Nephrol 80:25-29. Abstract Only.

Kopp UC, Smith LA (1987) Renorenal reflex responses to renal sensory receptor stimulation in normotension and hypertension. Clin Exp Hypertens A 9 Suppl 1:113-125.

Kopp UC, Olson LA, DiBona GF (1984) Renorenal reflex responses to mechano- and chemoreceptor stimulation in the dog and rat. Am J Physiol 246:F67-77.

Kopp UC, Jones SY, DiBona GF (2008) Afferent renal denervation impairs baroreflex control of efferent renal sympathetic nerve activity. Am J Physiol Regul Integr Comp Physiol 295:R1882-1890.

Kopp, U. C.: "Nerual Control of Renal Function," University of Iowa Carver College of Medicine, Department of Veterans Affairs Medical Center, San Rafael, CA, 2011. Abstrat Only.

Lang RJ, Davidson ME, Exintaris B (2002) Pyeloureteral motility and ureteral peristalsis: essential role of sensory nerves and endogenous prostaglandins. Exp Physiol 87:129-146.

Lazzeri M, Barbanti G, Beneforti P, Maggi CA, Taddei I, Andrea U, Cantini C, Castellani S, Turini D (1995) Vesical-renal reflex: diuresis and natriuresis activated by intravesical capsaicin. Scand J Urol Nephrol 29:39-43.

Li J, Wang DH (2008) Increased GFR and renal excretory function by activation of TRPV1 in the isolated perfused kidney. Pharmacol Res 57:239-246.

Ma MC, Huang HS, Chen CF (2002) Impaired renal sensory responses after unilateral ureteral obstruction in the rat. J Am Soc Nephrol 13:1008-1016.

Ma MC, Huang HS, Chen YS, Lee SH (2008) Mechanosensitive N-methyl-D-aspartate receptors contribute to sensory activation in the rat renal pelvis. Hypertension 52:938-944.

Melick WF, Brodeur AE, Herbig F, Naryka JJ (1966) Use of a ureteral pacemaker in the treatment of ureteral reflux. J Urol 95:184-196.

Ming Z, Smyth DD, Lautt WW (2002) Decreases in portal flow trigger a hepatorenal reflex to inhibit renal sodium and water excretion in rats: role of adenosine. Hepatology 35:167-175.

Office Action issued Jul. 30, 2012 for Australian Patent Application No. 2009325847.

Palla R, Parrini M, Panichi V, Andreini B, De Pietro S, Migliori M, Bianchi AM, Giovannini L, Bertelli A, Bertelli AA, et al. (1995) Acute effects of calcitonin gene related peptide on renal haemodynamics and renin and angiotensin II secretion in patients with renal disease. Int J Tissue React 17:43-49.

Petersson M, Friberg P, Eisenhofer G, Lambert G, Rundqvist B (2005) Long-term outcome in relation to renal sympathetic activity in patients with chronic heart failure. Eur Heart J 26:906-913.

Petkov P (1975) Electrostimulation of the ureter as a treatment method in ureteral calculi. Khirurgiia (Sofiia) 28:292-294. Bulgarian Edition only.

Polsky A, Mel B, Schiller J (2009) Encoding and decoding bursts by NMDA spikes in basal dendrites of layer 5 pyramidal neurons. J Neurosci 29:11891-11903.

Ronco C, Chionh CY, Haapio M, Anavekar NS, House A, Bellomo R (2009) The cardiorenal syndrome. Blood Purif 27:114-126.

Schlaich MP, Sobotka PA, Krum H, Whitbourn R, Walton A, Esler MD (2009) Renal Denervation as a Therapeutic Approach for Hypertension: Novel Implications for an Old Concept. Hypertension 54:1195-1201.

Schramm LP, Carlson DE (1975) Inhibition of renal vasoconstriction by elevated ureteral pressure. Am J Physiol 228:1126-1133.

Shekhar YC, Anand IS, Sarma R, Ferrari R, Wahi PL, Poole-Wilson PA (1991) Effects of prolonged infusion of human alpha calcitonin gene-related peptide on hemodynamics, renal blood flow.

Tsuchida S, Kumagai I (1978) Effect of urinary bladder distension on renal blood flow, blood pressure and plasma renin activity. Tohoku J Exp Med 126:335-341.

Van Balken MR, Vergunst H, Bemelmans BL (2004) The use of electrical devices for the treatment of bladder dysfunction: a review of methods. J Urol 172:846-851.

Walter JS et al. Evaluation of direct bladder stimulation with stainless steel woven eye electrodes. J. Urol. Dec. 1993; 150(6): 1990-69 with Abstract.

Xie C, Sachs JR, Wang DH (2008) Interdependent regulation of afferent renal nerve activity and renal function: role of transient receptor potential vanilloid type 1, neurokinin 1, and calcitonin gene-related peptide receptors. J Pharmacol Exp Ther 325:751-757.

Zhu Y, Wang Y, Wang DH (2005) Diuresis and natriuresis caused by activation of VR1-positive sensory nerves in renal pelvis of rats. Hypertension 46:992-997.

Zhu Y, Xie C, Wang DH (2007) TRPV1-mediated diuresis and natriuresis induced by hypertonic saline perfusion of the renal pelvis. Am J Nephrol 27:530-537.

An Office Action dated Nov. 18, 2013, which issued during the prosecution of U.S. Appl. No. 13/156,753.

Miller, "Management of the Patient with Anuria". (May 19, 1949) Proceedings of the Royal Society of Medicine, vol. XLII, p. 801-805, Section of Urology.

Chinese Office Action for Chinese Patent Application No. 200980156494.X dated Jul. 1, 2013; including English Translation of the Office Action.

* cited by examiner

STIMULATION OF THE URINARY SYSTEM

CROSS REFERENCES TO RELATED APPLICATIONS

The present application:
(a) is a continuation-in-part of U.S. Ser. No. 13/156,753 to Bar-Yoseph (published as US 2011/0301662), which:
  (i) is a continuation-in-part of PCT Application PCT/IL2009/001163 to Bar-Yoseph (published as WO 10/067360), filed Dec. 9, 2009, which claims the benefit of:
    U.S. Provisional Application 61/120,901, filed Dec. 9, 2008;
    U.S. Provisional Application 61/173,228, filed Apr. 28, 2009;
    U.S. Provisional Application 61/180,957 filed on May 26, 2009;
    U.S. Provisional Application 61/218,139, filed Jun. 18, 2009;
    U.S. Provisional Application 61/225,226, filed on Jul. 14, 2009; and
    U.S. Provisional Application 61/233,500, filed on Aug. 13, 2009; and
  (ii) claims the benefit of U.S. Provisional Application 61/355,522, filed Jun. 16, 2010; and
(b) claims the benefit of U.S. Provisional Application 61/451,406 to Bleicher, filed Mar. 10, 2011.

All of the above-referenced applications are incorporated herein by reference.

FIELD OF EMBODIMENTS OF THE INVENTION

Some applications of the present invention generally relate to apparatus and methods for modifying bodily functions. Specifically, some applications of the present invention relate to stimulating the urinary system.

BACKGROUND

The kidneys are organs that have numerous biological roles. Their primary role is to maintain the homeostatic balance of bodily fluids by filtering and secreting metabolites and minerals from the blood and excreting them, along with water, as urine. The ureters are muscular ducts that propel urine from the kidneys to the urinary bladder. In the adult, the ureters are usually 25-30 cm (10-12 inches) long.

Congestive heart failure (CHF) is a very common disorder, affecting 6 million Americans and more than 22 million worldwide. CHF is the leading hospital discharge diagnosis in individuals aged 65 years or older. Renal impairment is an independent and significant predictor of morbidity and mortality in CHF patients. Mortality increases incrementally across the range of renal function, with 7% increased risk for every 10-mL/min decrease in glomerular filtration rate (GFR). CHF triggers kidney dysfunction by a pathological process dubbed the cardio-renal syndrome. The cardio-renal syndrome can be acute, characterized by a rapid decrease in cardiac output together with worsening renal function or chronic, in which gradual worsening of heart and/or kidney function develops over months.

The cardio-renal syndrome is a common condition. In the US, more than 500,000 patients are admitted to hospital every year with acute heart failure, and up 80% of these patients suffer from deteriorating renal functions. High renal sympathetic activity constitutes a link between CHF and renal dysfunction. Signals of shock and hypoperfusion present in CHF patients, activate a number of compensation systems to increase the blood pressure and prevent fluid losses. Of these, the renal sympathetic system is one of the most important ones. The renal sympathetic system effectively reduces renal blood flow and kidney functions, including sodium and water excretion to urine. In addition, the renal sympathetic system activates the renin-angiotensin-aldosterone axis and therefore leads to hypertension, fluid retention and kidney dysfunction. Increased renal sympathetic drive has been described as being a factor in causing progressive deterioration of renal function and adverse outcome in CHF patients, in an article by Petersson et al., entitled "Long-term outcome in relation to renal sympathetic activity in patients with chronic heart failure" (European Heart Journal (2005) 26, 906-913).

Hypertension is one of the most common worldwide diseases afflicting humans. In the US, forty-three million people are estimated to have hypertension, the age-adjusted prevalence of hypertension varying from 18-32%. Abnormal renal excretory function is a mechanism associated with the initiation and progression of hypertension. Variations of arterial pressure signals the kidney to alter urinary sodium and water excretion. In the long term, maintenance of sodium and water balance by the kidneys is believed to be an important factor in the long-term control of arterial pressure. Thus, factors that decrease renal excretory function lead to an increase in arterial pressure, which is required to reestablish and maintain sodium and water balance.

Chronic kidney disease (CKD) is a major cause of morbidity and mortality, particularly at later stages of the disease. There is evidence to indicate the presence of functional abnormalities of the sympathetic nervous system in uremic animals and humans. In patients with bilateral nephrectomy, the rate of sympathetic discharge is lower than in patients with their native kidneys, and this increased rate is accompanied by lower mean arterial pressure and regional vascular resistance.

Sympathetic activation contributes to progressive kidney damage by elevation of blood pressure and by promoting atherosclerosis. Increased sympathetic activity, progressive atherosclerosis and elevated blood pressure contribute to the development of cardiac remodeling and functional alterations. These conditions are highly prevalent in patients with CKD.

Causes of acute renal failure (ARF) can be broadly divided into three clinical categories: a) Prerenal, which is an adaptive response to severe volume depletion b) renal (or intrinsic), in response to kidney insult, including contrast material, and c) postrenal.

Prerenal ARF is the most common cause of ARF. It often leads to intrinsic ARF if it is not promptly corrected. Acute reduction of renal blood flow (RBF), either because of blood loss or hypotension can result in this syndrome. The hallmark of intrinsic ARF and the most common form is acute tubular injury (ATN). Prerenal ARF and ATN occur on a continuum of the same pathophysiological process and together account for 75% of the cases of ARF.

Mortality rate estimates in ARF patients vary from 25-90%. The in-hospital mortality rate is 40-50%; in intensive care settings, the rate is 70-80%. The mortality in patients requiring dialysis is about 50%. Mortality rates have changed little over the last two decades, reflecting the fact that there is no adequate treatment for this condition.

SUMMARY OF EMBODIMENTS

For some applications of the present invention, a structure is inserted inside a subject's bladder. The bladder is mechanically stimulated by moving the structure with respect to an inner wall of the bladder, while at least a portion of the structure is contacting the inner wall.

For some applications, a device having an expandable distal portion thereof is inserted into the bladder, and/or into a different portion of the subject's body. For example, a transurethral catheter having a balloon disposed on a distal portion thereof may be inserted into the subject's bladder, via the subject's urethra. At least one protruding member is disposed on the distal portion of the device (e.g., on the balloon). For example, mechanical protruding members, and/or electrical contacts may protrude from the balloon. A protruding-member-protection layer is disposed at the distal portion of the device. For example, an outer balloon, a patch, and/or a covering sheath may be disposed on at least a portion of the outer surface of the balloon.

When the distal portion of the device is in a contracted state thereof (e.g., when the balloon is in a deflated state), the protruding member does not protrude from the protruding-member-protection layer. When the distal portion is in an expanded state thereof (e.g., when the balloon is in an inflated state), the protruding member at least partially protrudes from the protruding-member-protection layer.

For some applications, when the balloon is deflated, the outer surfaces of the protruding members are flush with the outer surface of the protruding-member-protection layer. Alternatively, the protruding-member-protection layer covers at least a portion of, or the whole of, the outer surface of the protruding member, when the inner balloon is in the deflated state. Thus, during insertion of the catheter via the subject's urethra, the protruding-member-protection layer reduces damage and/or discomfort to the subject's urethra resulting from the protruding member rubbing and/or scratching the urethra. Alternatively or additionally, during insertion of the catheter via the subject's urethra, the protruding-member-protection layer protects the protruding member from being damaged and/or from becoming decoupled from the balloon.

For some applications, apparatus is provided for stimulating the urinary system, including (a) at least one elongate element configured to lie within the ureter, allowing free urine flow within the ureter and configured to not interfere with operation of ureter valves, (b) at least one stimulator element mechanically coupled to the elongate element, and (c) a controller configured to stimulate the at least one stimulator element with a stimulation sequence suitable to modify a function of at least one kidney or a cardiovascular system. Optionally, the stimulator element includes an expandable element, and/or the stimulator element is configured to expand past a resting diameter of a ureter. For some applications, the stimulator element includes one or more of a mechanical stimulator, a chemical stimulator and a thermal stimulator. For some applications, the element is thin enough and soft enough to not interfere with operation of ureter valves. For some applications, the stimulator contact is in the form of a tubular element of at least 3 mm in length mounted on an elongate element of at least 20 cm in length, which apparatus lodges in a ureter or renal pelvis. Alternatively or additionally, the stimulator contact is in the form of a conical element that lodges in a renal pelvis. For some applications, the elongate element is adapted for an insertion via a nephrostomic route.

There is therefore provided, in accordance with some applications of the present invention, apparatus, including:
a device having an expandable distal portion thereof;
at least one protruding member disposed on the distal portion of the device; and
a protruding-member-protection layer disposed at the distal portion of the device, and configured such that:
when the distal portion is in a contracted state thereof, the protruding member does not protrude from the protruding-member-protection layer, and
when the distal portion is in an expanded state thereof, the protruding member at least partially protrudes from the protruding-member-protection layer.

For some applications, the protruding-member-protection layer includes a covering sheath that is placed over a portion of an outer surface of the expandable distal portion, the outer surface of the expandable distal portion is shaped to define an indentation that conforms with a shape of the covering sheath, and the covering sheath is configured such that when the covering sheath is placed inside the indentation, an outer surface of the covering sheath is flush with the outer surface of the expandable distal portion adjacent to the covering sheath.

For some applications, the protruding-member-protection layer includes a patch that is placed over a portion of an outer surface of the expandable distal portion.

For some applications, the at least one protruding member includes two to twenty protruding members.

For some applications, when the distal portion is in the contracted state thereof, the protruding-member-protection layer is configured to be flush with outer surfaces of the protruding member.

For some applications, when the distal portion is in the contracted state thereof, the protruding-member-protection layer is configured to at least partially cover the protruding member.

For some applications, the protruding-member-protection layer defines a hole, through which the protruding member protrudes when the distal portion is in the expanded state thereof, and edges of the protruding-member-protection layer that are adjacent to the hole are thickened with respect to other portions of the protruding-member-protection layer.

For some applications, even when the distal portion is in the expanded state, the protruding-member-protection layer partially covers the protruding member.

For some applications, the protruding member is shaped to define an outer rim and an inner thickened region, and, when the distal portion is in the expanded state, the protruding-member-protection layer at least partially covers the outer rim of the protruding member.

For some applications, the expandable distal portion includes an inflatable balloon.

For some applications, the protruding-member-protection layer includes an outer balloon disposed over the inflatable balloon, the outer balloon being configured to be stretched by the inner balloon, when the inner balloon is in the expanded state, such that the protruding member protrudes from the outer balloon.

For some applications, at least a portion of the inflatable balloon includes inner and outer layers, the inner and outer layers defining a slit therebetween, the protruding member is disposed inside the slit, and the outer layer includes the protruding-member-protection layer.

For some applications, the inner and outer layers are configured to fixate the protruding member with respect to the balloon by squeezing the protruding member therebetween.

For some applications, the balloon is configured to be inflated to a volume of more than 30 cc.

For some applications, the balloon is configured to be inflated to a volume of more than 50 cc.

For some applications, the balloon is configured to be inflated to a volume of more than 100 cc.

For some applications, the distal portion of the device is configured to be inserted into a body of a subject via a lumen of the subject, and:
during the insertion, the distal portion of the device is configured to be in the contracted state; and
when the distal portion of the device is inside the subject's body, the distal portion is configured to be expanded.

For some applications, the device includes a transurethral catheter, and the distal portion of the device is configured to be inserted into a bladder of the subject via a urethra of the subject.

For some applications, the catheter includes a catheter shaft, a length of the catheter shaft being between 5 cm and 150 cm.

For some applications, the catheter includes a flexible catheter shaft.

For some applications, the catheter defines a urine-drainage port at the distal portion, the port being configured to facilitate drainage of urine from the bladder, via the catheter.

For some applications, the protruding member includes an electrical contact, the apparatus further including a control unit configured to electrically stimulate the subject's bladder by driving a current into the subject's bladder via the electrical contact.

For some applications, the protruding member includes a mechanical member configured to mechanically stimulate the subject's bladder by being moved with respect to an inner wall of the bladder.

There is further provided, in accordance with some applications of the present invention, apparatus, including:
a balloon including a balloon material;
at least one protruding member configured to protrude from an outer surface of the balloon when the balloon is in an inflated state thereof, the protruding member being shaped to define a hollow space therein,
the protruding member being coupled to the balloon by a portion of the balloon material being molded within the hollow space.

For some applications, the protruding member includes a mushroom-shaped protruding member.

For some applications, the protruding member is shaped to define anchoring portions that are embedded within the balloon material.

For some applications, the protruding member is shaped to define at least one hole therethrough, the protruding member being coupled to the balloon by a portion of the balloon material being molded through the hole.

For some applications, the protruding member is shaped to define at least two holes therethrough, the holes crossing with one another, the protruding members being coupled to the balloon by a portion of the balloon material being molded through the holes.

There is additionally provided, in accordance with some applications of the present invention, apparatus, including:
an elongate element, a distal portion of which is configured to be inserted into a subject's body; and
a balloon disposed at the distal portion of the elongate element,
the balloon being configured to have inflated and deflated states thereof,
respective regions of the balloon including material having respective characteristics, such that, in the inflated state, the balloon defines a non-uniform outer surface.

For some applications, the balloon is configured to be inserted inside a subject's bladder and to mechanically stimulate the subject's bladder by moving with respect to an inner wall of the subject's bladder.

For some applications, the balloon is configured such that in the inflated state, the outer surface of the balloon is ridged.

For some applications:
the balloon includes a first set of regions and a second set of regions, the first set of regions being more stretchable than the second set of regions,
in the deflated state of the balloon, the first set of regions and the second set of regions are of equal thickness, and
when the balloon is inflated, the first set of regions stretch more than the second set of regions, causing the second set of regions to protrude from an outer surface of the balloon defined by the first set of regions, when the balloon is in the inflated state thereof.

For some applications, the balloon includes a silicone balloon and the first and second set of regions include silicone having respective durometers.

For some applications, the second set of regions includes two to twenty non-contiguous regions that are configured to protrude from the outer surface of the balloon defined by the first set of regions, when the balloon is in the inflated state thereof.

For some applications, when the balloon is in the inflated state, each of the regions of the second set of regions is separated from an adjacent region of the second set of regions by a distance of at least 1 mm.

There is further provided, in accordance with some applications of the present invention, a method, including:
identifying a subject as suffering from an impaired body system, the body system being selected from the group consisting of: a cardiovascular system and a renal system; and
in response thereto:
inserting a structure inside a bladder of the subject; and
mechanically stimulating the bladder with the structure.

For some applications, inserting the structure into the bladder includes inserting a balloon into the bladder.

For some applications, inserting the structure into the bladder includes inserting a stiff mechanical element into the bladder.

For some applications, mechanically stimulating the bladder with the structure includes moving the structure using an engine.

For some applications, mechanically stimulating the bladder with the structure includes moving the structure magnetically.

For some applications, mechanically stimulating the bladder includes controlling a kidney function of the subject selected from the group consisting of: glomerular filtration rate, urine flow rate, urine composition, urine density and renal hormone secretion.

For some applications, mechanically stimulating the bladder includes controlling a cardiovascular function of the subject selected from the group consisting of: blood pressure, portal pressure, pulmonary pressure, organ blood flow, cardiac output, heart rate, intravascular fluid volume, extravascular fluid volume, pulmonary edema level, and body edema level.

For some applications, inserting the structure inside the subject's bladder includes inserting a catheter into the bladder, the structure being disposed at a distal end of a catheter, and inserting the catheter includes facilitating outflow of urine from the bladder via a urine-drainage lumen of the catheter.

For some applications, the method further includes detecting a parameter of the subject, and mechanically stimulating the bladder includes mechanically stimulating the bladder responsively to the detected parameter.

For some applications, detecting the parameter includes detecting impedance of the subject's urine.

For some applications, detecting the parameter includes detecting a parameter selected from the group consisting of: glomerular filtration rate, urine flow, urine composition, secretion of hormones from the kidney, a creatinine level, and an insulin level.

For some applications, detecting the parameter includes detecting a parameter selected from the group consisting of: a urinary parameter, urinary peristalsis, and urinary pressure.

For some applications, detecting the parameter includes detecting a parameter selected from the group consisting of: blood chemistry, blood pressure, heart rate, breathing rate, lung fluid volume, and ECG.

For some applications, mechanically stimulating the bladder with the structure includes moving the structure with respect to an inner wall of the bladder, while at least a portion of the structure is contacting the inner wall.

For some applications, the structure includes a structure disposed at an end of a transurethral catheter, and moving the structure includes performing an action selected from the group consisting of: vibrating the catheter, pushing the catheter, pulling the catheter, and modulating a length of the catheter.

For some applications, the structure includes a device that is configured to remain inside the subject's bladder in the absence of a transurethral catheter, and moving the structure includes moving the device.

For some applications, moving the structure includes directing energy toward the structure from a location outside a body of the subject.

For some applications, directing energy toward the structure includes directing a magnetic field toward the structure.

For some applications, directing energy toward the structure includes directing waves toward the structure, the waves being selected from the group consisting of: sonic waves and ultrasonic waves.

For some applications, the structure includes a balloon, and moving the structure with respect to the inner wall of the bladder includes moving the balloon with respect to the inner wall of the bladder.

For some applications, the balloon includes protruding members that protrude therefrom, and mechanically stimulating the bladder includes moving the protruding members with respect to the inner wall of the bladder.

For some applications, moving the balloon with respect to the inner wall of the bladder includes modulating a volume of the balloon.

For some applications, modulating the volume of the balloon includes modulating the volume of the balloon at a frequency of 0.1 Hz to 1 Hz.

For some applications, mechanically stimulating the bladder includes inflating the balloon to a volume of more than 30 cc.

For some applications, mechanically stimulating the bladder includes inflating the balloon to a volume of more than 50 cc.

For some applications, mechanically stimulating the bladder includes inflating the balloon to a volume of more than 100 cc.

There is additionally provided, in accordance with some applications of the present invention, a method, including:

identifying a subject as suffering from an impaired body system, the body system being selected from the group consisting of: a cardiovascular system and a renal system; and in response thereto, mechanically stimulating a bladder of the subject, by directing toward the subject's bladder waves selected from the group consisting of: sonic waves and ultrasonic waves.

The present invention will be more fully understood from the following detailed description of embodiments thereof, taken together with the drawings, in which:

DETAILED DESCRIPTION OF EMBODIMENTS

Figure 1A:
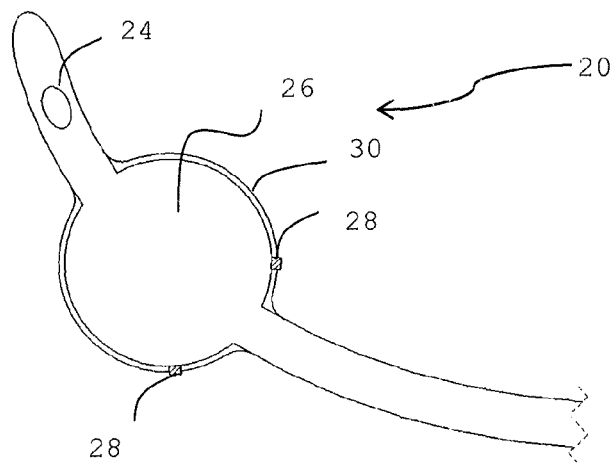
FIGS. 1A-D are schematic illustrations of a catheter that includes protruding members at a distal portion thereof, in accordance with some applications of the present invention.

Reference is now made to FIGS. 1A-D, which are schematic illustrations of a catheter 20 that includes protruding members 28 at a distal portion thereof, in accordance with some applications of the present invention. In accordance with some applications of the present invention, techniques are provided for at least partially covering the protruding members during insertion of the distal portion of the catheter into a subject's body, via a lumen of the subject's body. Typically, when the distal portion of the catheter is inside the subject's body, the protruding members are at least partially uncovered (in accordance with the techniques described hereinbelow) and are used to stimulate (e.g., mechanically and/or electrically stimulate) a portion of the subject's body, and/or to sense a parameter of a portion of the subject's body. For example, protruding members 28 may include electrical contacts, mechanical elements, an electrical sensor, a thermal energy source, an ultrasound probe, a thermal sensor, a pressure gauge, a drug-eluting structure, a degradable structure, and/or any type of sensor.

Typically, catheter 20 is used for stimulating a portion of a subject's bladder 22 (FIG. 1D) by being inserted into the bladder via the subject's urethra. For some applications, catheter 20 stimulates the subject's bladder in order control bodily functions such as kidney function, e.g., to control glomerular filtration rate (GFR), urine flow rate, urine composition, urine density and/or renal hormone secretion. Alternatively or additionally, catheter 20 stimulates the subject's bladder in order to control cardiovascular functions, such as blood pressure, portal pressure, pulmonary pressure, organ (including renal) blood flow, cardiac output, heart rate, intravascular and extravascular fluid volume, and/or pulmonary or body edema levels. For some applications, the catheter stimulates the subject's bladder in accordance with techniques described in PCT Application Publication WO 10/067360 to Bar-Yoseph, which is incorporated herein by reference. For some applications, the catheter stimulates the subject's bladder electrically and/or mechanically.

Typically, catheter 20 is placed inside the subject's bladder in order to provide an acute treatment while the subject is hospitalized, e.g., while the subject is suffering from CHF, hypertension, chronic kidney disease, and/or acute renal failure. For example, the catheter may be placed inside the subject's bladder for a period of more than one hour (e.g., more than five hours), and/or less than one month (e.g., less than one week). The catheter shaft is typically flexible, the length of the catheter shaft typically being more than 5 cm (e.g., more than 30 cm), and/or less than 150 cm (e.g., less than 50 cm).

For some applications, catheter 20 is inserted into a portion of the subject's body other than the bladder, and/or is inserted into the subject's body via a bodily lumen of the subject, or via a different portion of the subject's body, other than the urethra. For example, the catheter may be inserted into the subject's bladder via a suprapubic or a laparoscopic approach.

Typically, catheter 20 is an indwelling catheter. For example, the catheter may be generally similar to a Foley catheter. The catheter typically defines a drainage port 24 for draining urine from the subject's bladder. Urine flows into the drainage port from the subject's bladder. The urine typically drains out of the subject's body via a urine drainage lumen that is defined by the catheter shaft, as described hereinbelow. An inner balloon 26 is disposed at the distal end of the catheter. For some applications, the inner balloon is generally similar to the distal balloon of an indwelling bladder catheter, such as a Foley catheter. For some applications, balloon 26 is inflated to a maximum volume of more than 30 cc, e.g., more than 50 cc, more than 100 cc, or more than 250 cc (e.g., in order to facilitate mechanical stimulation of the bladder, as described hereinbelow). For some applications, a different expandable structure, such as a foam structure, or a mechanical structure (e.g., as described with reference to FIGS. 7A-C), is used instead of balloon 26.

Typically, one or more protruding members 28 protrude from the inner balloon. For example, the protruding members may include electrical contacts, via which the subject's bladder is electrically stimulated. Typically, for such applications, a control unit is disposed outside the subject's body (e.g., control unit 110 shown in FIG. 9) and/or is disposed inside the catheter shaft, the control unit electrically stimulating the bladder by driving a current into the inner wall of the bladder via the electrical contacts. Alternatively or additionally, the protruding members may be mechanical elements configured to mechanically stimulate the subject's bladder, e.g., by being pressed or rubbed against the subject's bladder. Further alternatively or additionally, protruding members 28 may include an electrical sensor, a thermal energy source, an ultrasound probe, a thermal sensor, a pressure gauge, a drug-eluting structure, a degradable structure, and/or any type of sensor. In accordance with respective applications, protruding members are portions of inner balloon 26 that are shaped so as to protrude (e.g., as described with reference to FIGS. 8A-B), and/or are separate members that are coupled to the inner balloon, e.g., in accordance with the coupling techniques described herein.

A protruding-member-protection layer is disposed on the outside of the inner balloon. For example, an outer balloon 30 may be disposed around inner balloon 26, and/or the inner balloon or a portion thereof may define a layer configured to act as the protruding-member-protection layer. The protruding-member-protection layer is configured to protect the subject's urethra during insertion of the catheter into the subject's bladder, by the protruding members not protruding from the layer during the insertion. For example, during the insertion, the protruding-member-protection layer may at least partially cover the protruding members, or may form a surface that is flush with outer surfaces of the protruding members. For some applications, the protruding-member-protection layer protects the protruding members from being damaged and/or from becoming decoupled from balloon 26 during insertion of the catheter into the subject's bladder.

Figure 1B:
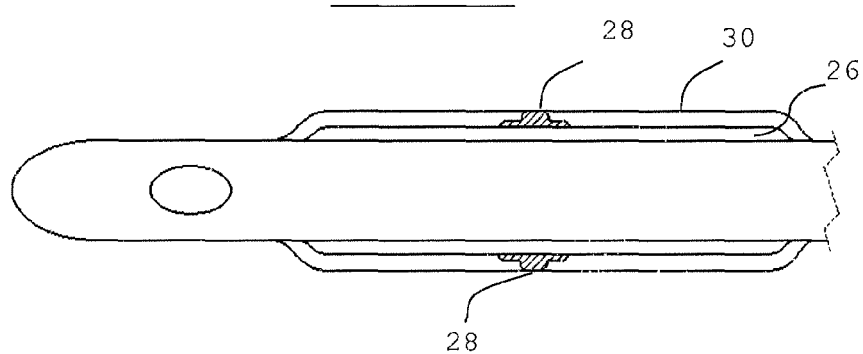
Figure 1C:
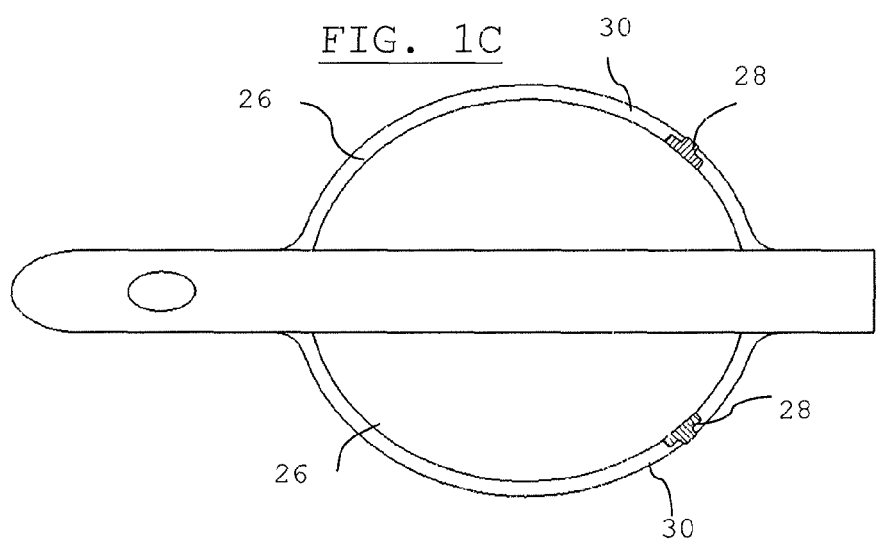
Figure 1D:
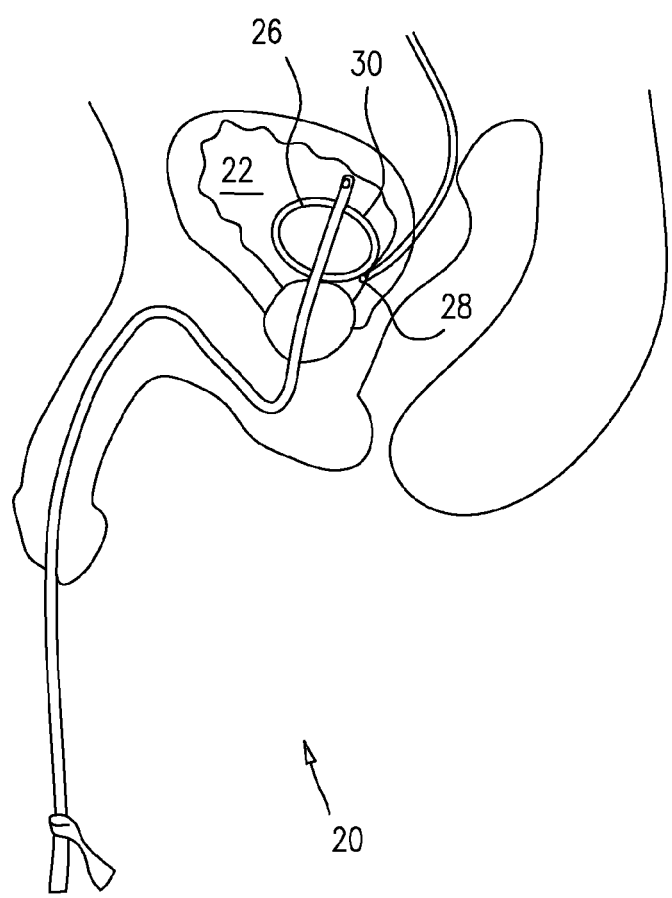

FIGS. 1B and 1C are, respectively, schematic illustrations of the distal end of catheter 20 when inner balloon 26 is in deflated and inflated states thereof. As shown in FIG. 1B, when the balloon is deflated, the outer surfaces of protruding members 28 are flush with the outer surface of outer balloon 30. (For some applications the outer balloon covers at least a portion of, or the whole of, the outer surface of the protruding member, when the inner balloon is in a deflated state.) Thus, during insertion of the catheter via the subject's urethra, the outer balloon reduces damage and/or discomfort to the subject's urethra resulting from the protruding member rubbing and/or scratching the urethra. Alternatively or additionally, during insertion of the catheter via the subject's urethra 32, the outer balloon protects the protruding member from being damaged and/or from becoming decoupled from balloon 26.

As shown in FIG. 1C, when inner balloon 26 is in an inflated state, outer balloon 30 stretches such that the outer surface of the outer balloon is no longer flush with the outer surfaces of the protruding members, and/or such that the outer balloon no longer covers the protruding members. Therefore, when the inner balloon is in an inflated state, protruding members 28 protrude from the outer surface of the outer balloon. Thus, the protruding members may be placed against the inner wall of the subject's bladder in order to stimulate bladder wall, e.g., electrically or mechanically.

Typically, upon deflating inner balloon 26, outer balloon 30 again forms a surface that is flush with outer Surfaces of protruding members 28 or that at least partially covers the protruding members, such that the protruding members do not protrude from the outer balloon. In this manner, the outer balloon reduces damage and/or discomfort to the subject's urethra resulting from the protruding member rubbing and/or scratching the urethra, during removal of the catheter from the subject's bladder, via the subject's urethra. Alternatively or additionally, the outer balloon protects the protruding member from being damaged and/or from becoming decoupled from balloon 26 during removal of the catheter from the subject's bladder, via the subject's urethra.

For some applications, protruding members 28 are used to apply stimulation (e.g., electrical or mechanical stimulation) to the trigone area of the subject's bladder. Alternatively, the protruding members are used to apply stimulation (e.g., electrical or mechanical stimulation) to a different area of the subject's bladder. For some applications, the protruding members are placed against the bladder wall and used to stimulate the bladder wall irrespective of the location of the protruding members with respect to the bladder wall. Typically, the number of protruding members that are used, and the placement of the protruding members with respect to inner balloon 26 are in accordance with the portion of the bladder wall that is to be stimulated. For some applications, two to twenty protruding members protrude from the balloon. Typically, when the balloon is in an inflated state, each of the protruding members is spaced from an adjacent protruding member by a distance of at least 1 mm.

For some applications, the techniques described herein for covering or otherwise protecting protruding members that protrude from a balloon, during insertion of the balloon into the subject's body via a bodily lumen, are applied to a balloon that is inserted into a portion of the subject's body other than the bladder, and/or is inserted into the subject's body via a bodily lumen of the subject, or via a different portion of the subject's body, other than the urethra. For some applications, the techniques described herein for covering or otherwise protecting protruding members that protrude from a medical instrument during insertion of the instrument into the subject's body via a bodily lumen are applied to medical instruments other than a balloon.

For example, the techniques described herein may be applied to a catheter that is inserted into a subject's heart, and that defines protruding members at a distal portion thereof. The protruding members may include sensors for sensing parameters of the subject's cardiac tissue, and/or electrical contacts for stimulating the subject's cardiac tissue. The protruding members do not protrude from protruding-member-protection layer during insertion of the catheter via a blood vessel of the subject. The protruding-member-protection layer facilitates protrusion of the protruding members from the distal portion of the catheter, when the distal portion of the catheter is disposed inside the subject's heart. Alternatively or additionally, the techniques described herein may be applied to a different medical instrument that defines protruding members at a distal portion thereof, and that is configured to be inserted into the subject's body via the subject's esophagus, trachea, vagina, anus, cervix, blood vessel, and/or another bodily lumen.

Figure 2A:
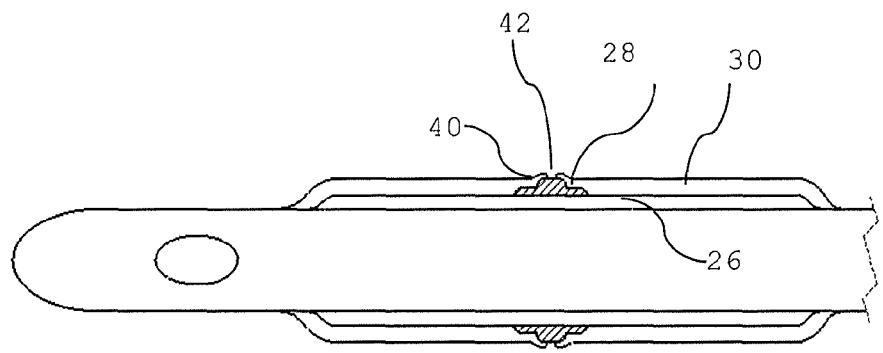
FIGS. 2A-D are schematic illustrations of an outer balloon of a catheter, the outer balloon defining holes, via which protruding members protrude through the outer balloon, in accordance with some applications of the present invention.
Figure 2B:
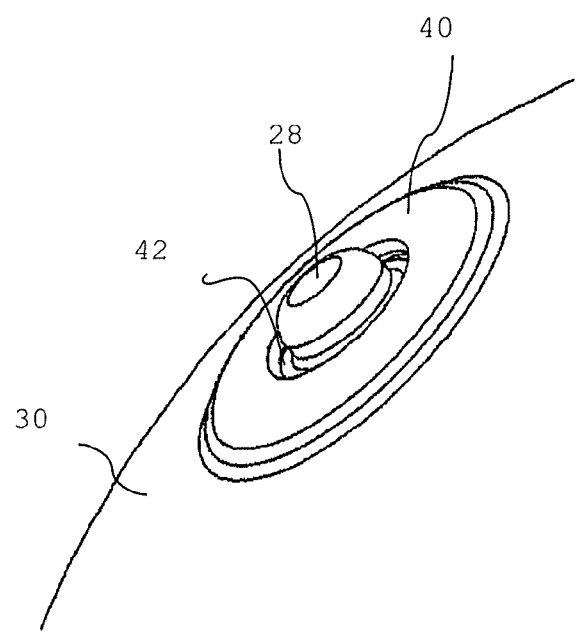

Reference is now made to FIGS. 2A-D, which are schematic illustrations of outer balloon 30 of catheter 20, the outer balloon defining holes 42, via which protruding members protrude through the outer balloon, in accordance with some applications of the present invention. Typically, inner balloon 26 (shown in FIGS. 1A-D) and outer balloon 30 are made of silicone, and/or another stretchable material, such as polyurethane, or a different flexible thermoplastic. As shown in FIGS. 2A-B, the outer balloon defines holes 42, through which the protruding members protrude when the inner balloon is in an inflated state. Edges 40 of the outer balloon that define holes 42 are thickened with respect to portions of the outer balloon that are not adjacent to the protruding members (e.g., by the edges being made of silicone of a higher durometer than the other portions of the balloon). For example, the edges may be thickened in order to reduce the likelihood of the edges tearing, when the outer balloon is stretched, by inner balloon 26 being inflated. Alternatively or additionally, the thickened edges may be such as to raise the outer surface of the outer balloon in the regions of the outer balloon adjacent to the protruding members, such that the regions of the outer balloon adjacent to the protruding members are flush with the protruding members, when the inner balloon is in a deflated state. For some applications, when the inner balloon is in a deflated state, edges 40 of hole 42 are above the outer surface of protruding member 28.

Figure 2C:
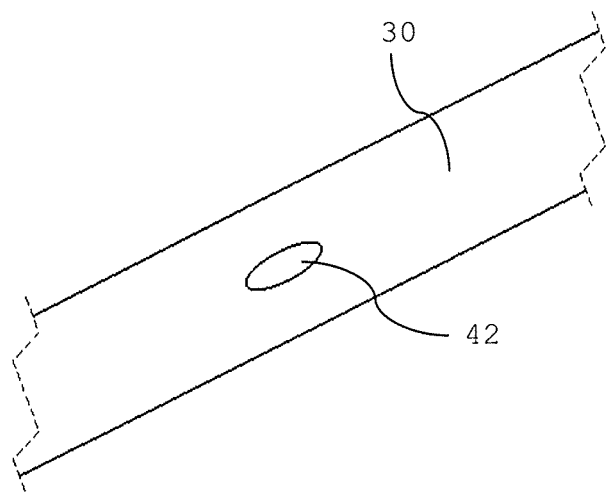
Figure 2D:
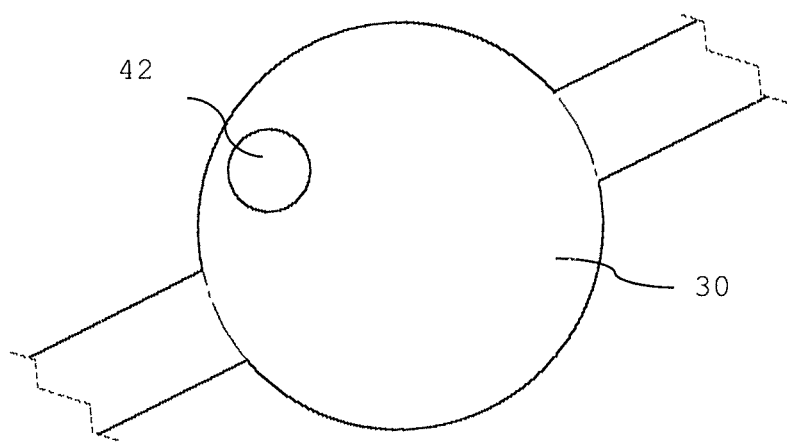

For some applications, when the outer balloon is not stretched, holes 42 are non-circular, e.g., elliptical, or the shape of a racetrack, as shown in FIG. 2C. Typically, when the outer balloon is stretched (by the inner balloon being inflated), the outer balloon stretches circumferentially more than the balloon stretches longitudinally. Thus, when the outer balloon is stretched (by the inner balloon being inflated), holes 42 become generally circular, as shown in FIG. 2D. The generally circular shape of the holes when balloon 26 is in an inflated state, is typically such as to facilitate protrusion of the protruding members through the holes. In general, holes 42 are shaped such as to facilitate protrusion of the protruding members through the holes, when balloon 26 is in an inflated state.

Figure 3A:
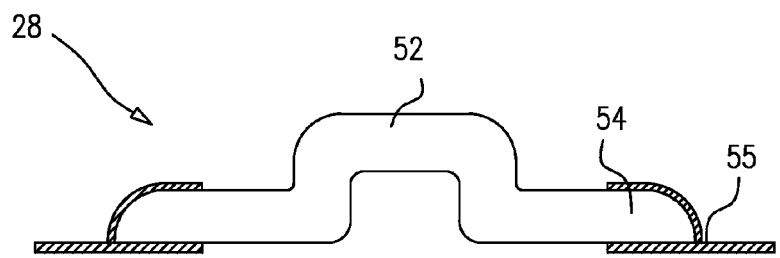
FIGS. 3A-C are schematic illustrations of a protruding member that facilitates at least partial covering of the protruding member by the outer balloon when the inner balloon is deflated, in accordance with some applications of the present invention.
Figure 3B:
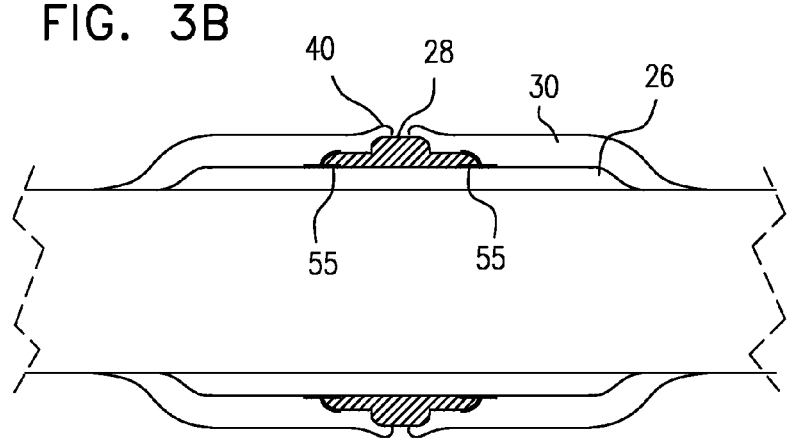
Figure 3C:
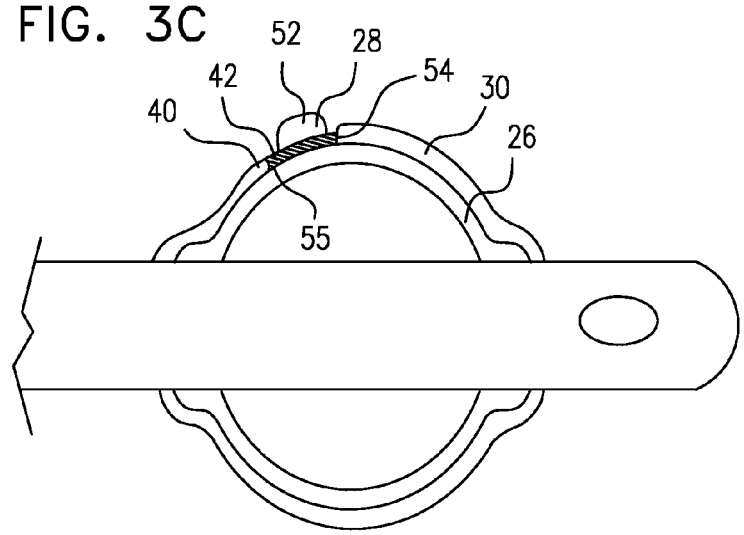

Reference is now made to FIGS. 3A-C, which are schematic illustrations of a protruding member 28 that facilitates at least partial covering of the protruding member 28 by outer balloon 30, even when inner balloon 26 is inflated, in accordance with some applications of the present invention. Protruding member 28, as shown in FIGS. 3A-C, defines a central thick portion 52, and a thin outer rim 54. For some applications, a ring-shaped film 55 of kapton, or a similar material, surrounds the protruding member.

FIGS. 3B and 3C show inner balloon 26 and outer balloon 30, when inner balloon is, respectively, in deflated and inflated states thereof. As shown in FIG. 3C, when inner balloon 26 is inflated (thereby stretching outer balloon 30), a portion of protruding member 28 (e.g., a portion of rim 54) is covered by outer balloon 30, and a portion of protruding member 28 (e.g., portion 52) protrudes from the outer balloon. For some applications, the partial covering of the protruding member by the outer balloon, even when the inner balloon is in an inflated state, reduces the likelihood of the edges 40 of the outer balloon adjacent to the protruding members sliding underneath the protruding members, during deflation of the inner balloon. As shown in FIG. 3B, when the inner balloon is deflated, the outer balloon typically covers a portion of central portion 52 of protruding member 28, as well as covering rim 54. As described hereinabove, typically, edges 40 of holes 42 (through which the protruding members protrude) are thickened with respect to other portions of outer balloon 30.

For some applications, ring-shaped film 55 is electrically non-conductive and is placed around protruding member 28 in order to electrically isolate the protruding member (e.g., when the protruding member is an electrical contact). Alternatively or additionally, the ring-shaped film reduces the likelihood of edges 40 of the outer balloon adjacent to the protruding members sliding underneath the protruding members, during deflation of the inner balloon.

Figure 4A:
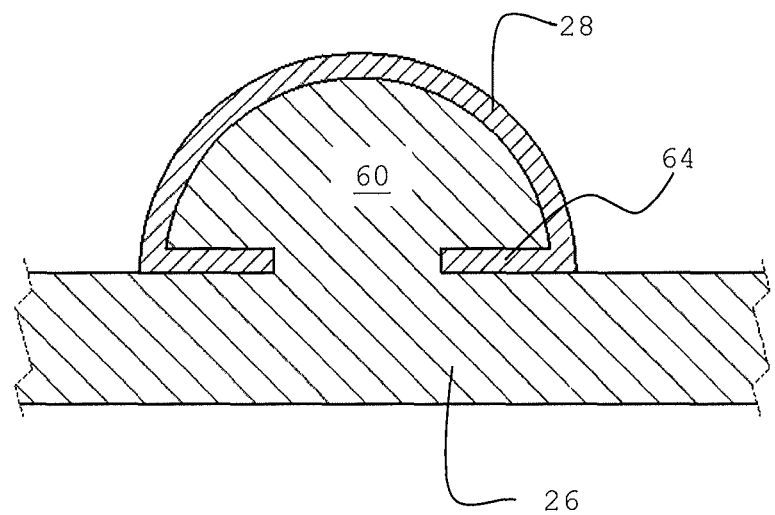
FIGS. 4A-B are schematic illustrations of a protruding member that is coupled to a balloon using a coupling technique, in accordance with some applications of the present invention.
Figure 4B:
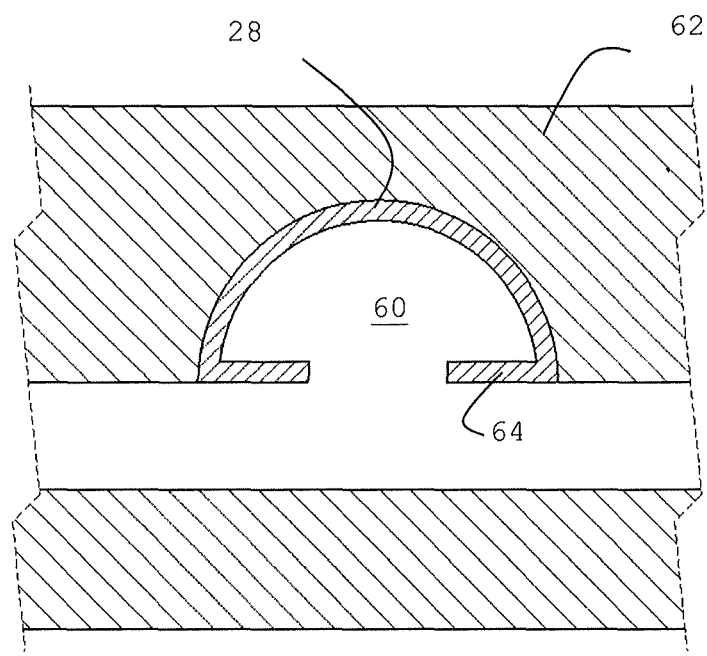

Reference is now made to FIGS. 4A-B, which are schematic illustrations of protruding member 28, the protruding member being coupled to inner balloon 26, in accordance with some applications of the present invention. It is noted that, for some applications, protruding members 28 are coupled to inner balloon 26 using an adhesive, such as a cyanoacrylate adhesive, and/or silicone adhesive. Alternatively or additionally, the protruding members are coupled to inner balloon 26 using techniques that do not require the use of an adhesive, e.g., using the techniques described with reference to FIGS. 4A-6C. For some applications the techniques described with reference to FIGS. 4A-6C are used to couple protruding members to a balloon, in addition to using an adhesive to facilitate the coupling.

For some applications, coupling the protruding members to inner balloon 26 using coupling techniques in addition to, or as an alternative to, using an adhesive, reduces the likelihood of the protruding members becoming decoupled from the inner balloon when the inner balloon is inflated, relative to if the protruding members are coupled to the inner balloon using only an adhesive. For some applications, not using adhesive to couple the protruding members to the balloon reduces the overall thickness of the balloon and the protruding members.

FIG. 4A shows balloon 26 coupled to protruding member 28. Typically, balloon 26 is formed by injection-molding a material such as silicone into a mold. FIG. 4B shows a portion of a mold 62 that is used for molding balloon 26. As shown in FIGS. 4A-B, for some applications, protruding member 28 is mushroom-shaped, the protruding member defining a hollow space 60. During the molding process, protruding member is placed inside an indent in the mold. The silicone (or other material) enters hollow space 60, which is defined by the protruding member, such that silicone is disposed inside the hollow space. As shown, protruding member 28 defines anchoring portions 64. The anchoring portions anchor the protruding member to the balloon, the balloon material (e.g., the silicone) being disposed above and below the anchoring portions, thereby embedding the anchoring portions inside the balloon material. For some applications, the anchoring portions facilitate coupling of the protruding member to the balloon without requiring the use of an adhesive. Alternatively, the anchoring portions are used in addition to an adhesive, to facilitate coupling of the protruding member to the balloon.

Figure 5A:
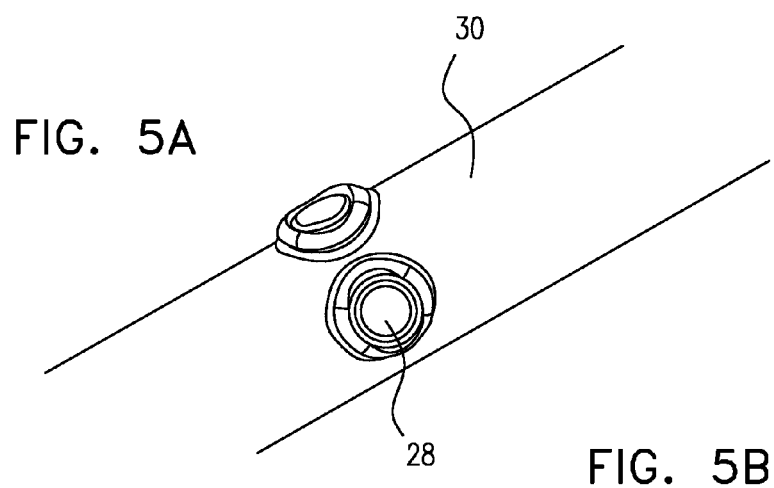
FIGS. 5A-D are schematic illustrations of a protruding member that is coupled to a balloon using a coupling technique, in accordance with some alternative applications of the present invention.
Figure 5B:
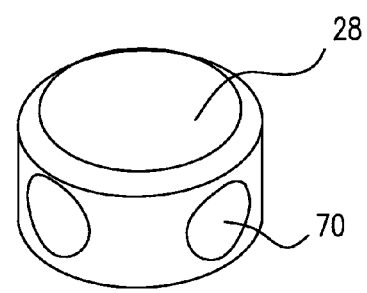

Reference is now made to FIGS. 5A-D, which are schematic illustrations of protruding member 28, the protruding member being coupled to outer balloon 30 using a coupling technique, in accordance with some alternative applications of the present invention. It is noted that for some applications, protruding member 28, as shown in FIGS. 5A-D, is coupled to inner balloon 26. For such applications, an outer balloon may or may not be used with the inner balloon. For some applications, protruding member 28 defines hollow portions, e.g., holes 70 (as shown in FIG. 5B) that traverse the protruding member. For example, the protruding member may define two holes that cross with one another, or a different number of holes (e.g., between one and three holes). During molding of the outer balloon, silicone (or a different balloon material) flows through holes 70, and fills up the holes defined by the protruding member.

Figure 5C:
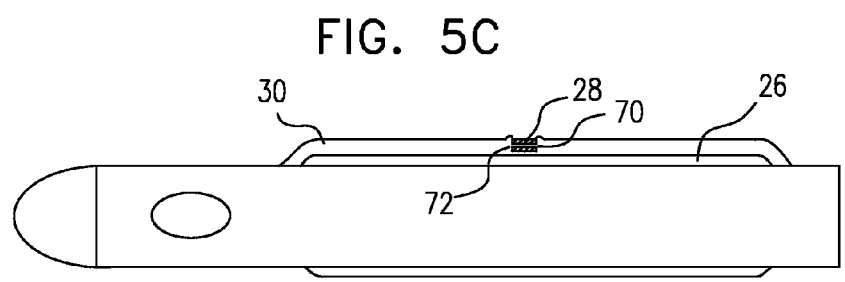
Figure 5D:
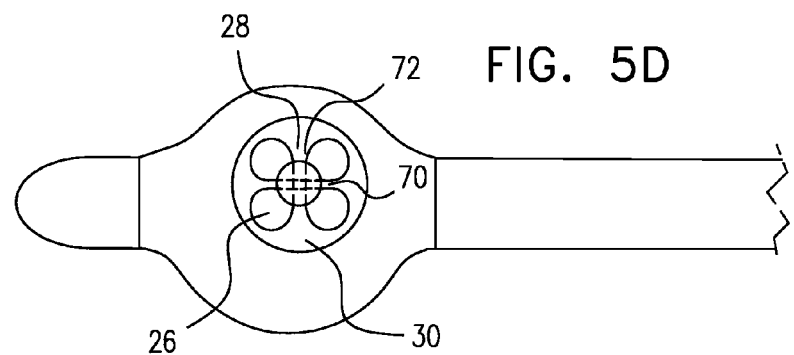

FIG. 5C is a cross-sectional view of protruding member 28 coupled to outer balloon 30, inner balloon 26 being in a deflated state. As shown, the outer surface of protruding member 28 does not protrude from the outer balloon. Also, as shown, a portion 72 of outer balloon passes through the protruding member via holes 70, thereby coupling the protruding member to the outer balloon. FIG. 5D shows protruding member 28 coupled to outer balloon 30, inner balloon 26 being in an inflated state. The outer surface of protruding member 28 protrudes from the outer surface of outer balloon 30. As shown, portions 72 of outer balloon pass through the protruding member via holes 70, thereby coupling the protruding member to the outer balloon.

Typically, the protruding members described with reference to FIGS. 4A-5D are used in conjunction with the techniques described herein for protecting the protruding members during the insertion of catheter 20 into the subject's body (e.g., by using a protruding-member-protection layer, such as outer balloon 30, as described hereinabove).

Figure 6A:
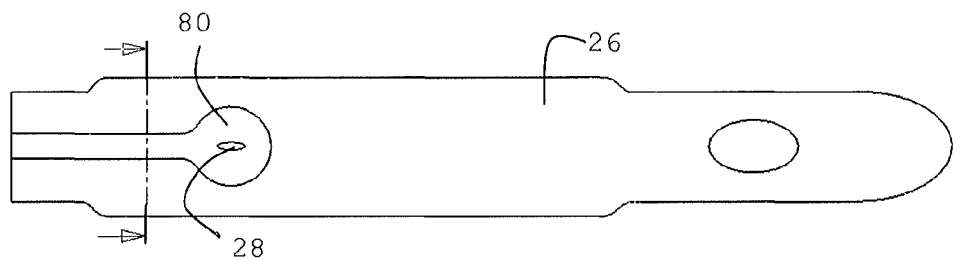
FIGS. 6A-C are schematic illustrations of a balloon configured for coupling a protruding member thereto, in accordance with some further alternative applications of the present invention.
Figure 6B:
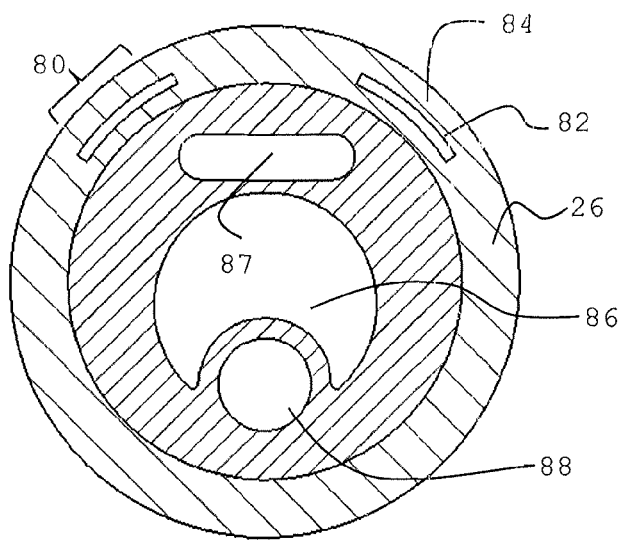
Figure 6C:
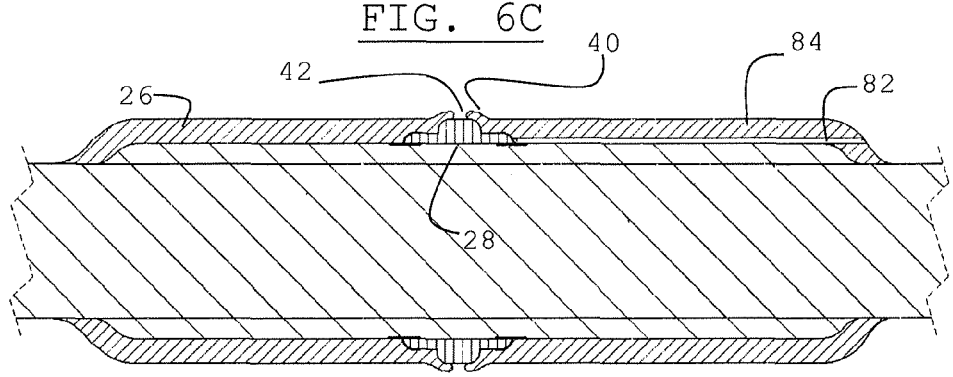

Reference is now made to FIGS. 6A-C, which are schematic illustrations of balloon 26, the balloon being configured for coupling protruding member 28 thereto, in accordance with some further alternative applications of the present invention. For some applications, rather than using an outer balloon to facilitate coupling of the protruding member to the inner balloon, and/or to protect the urethra during insertion of balloon 26 and protruding member 28 via the urethra, a portion 80 of balloon 26 is double-layered, the two layers of the balloon defining a slit 82 therebetween. Typically protruding member is inserted inside slit 82, as shown in FIG. 6C.

For some applications, an outer layer 84 of double-layered portion 80 of the balloon acts as protruding-member-protection layer, as described hereinabove. The outer layer protects the urethra during insertion of balloon 26 via the urethra, by at least partially covering the protruding member, and or by the outer surface of the outer layer being flush with the outer surface of the protruding member, such that the protruding member does not protrude from the outer layer. Alternatively or additionally, outer layer 84 protects the protruding member from being damaged and/or from becoming decoupled from balloon 26 during insertion of the catheter into the subject's bladder.

For some applications, protruding member 28 is squeezed into slit 82, between the inner and outer layers of the double-layered portion of the balloon. The inner and outer layers of the balloon squeeze the protruding member therebetween, thereby facilitating coupling of the protruding member to the balloon. For some applications, the squeezing of the protruding member between the inner and outer layers facilitates fixating the protruding member with respect to the balloon, e.g., such that the protruding member is disposed underneath hole 42, via which hole the protruding member protrudes when the balloon is inflated.

FIG. 6B shows a cross section view of the distal portion of catheter 20. As shown, for some applications the thickness of balloon 26 is generally similar in single-layered portions of the balloon to that of double-layered portion 80 of the balloon. For some applications, the thickness of the balloon is greater in the double-layered portion of the balloon than in single-layered portions of the balloon. For some applications (not shown), a portion of the catheter shaft is indented so as to accommodate a double-layered portion of the balloon that is thicker than single-layered portions of the balloon.

Typically, the catheter shaft of catheter 20 defines a urine-drainage lumen 86 to facilitate outflow of urine from the subject's bladder. The catheter shaft also defines an inflation lumen 87 to facilitate inflation of balloon 26. For some applications, protruding members 28 include electrical contacts that are connected to a control unit at the proximal end of the catheter via electrodes that pass through an electrode lumen 88, defined by the catheter shaft.

It is noted with respect to the techniques described with reference to FIGS. 4A-6C that, for some applications, the techniques are used for coupling a protruding member to a balloon that is inserted into portions of a subject's body other than a subject' bladder, and/or that is inserted via bodily lumens, or other portions of the subject's body, other than the subject's urethra, such as the subject's esophagus, trachea, vagina, anus, and/or blood vessel, e.g., as described hereinabove with reference to FIGS. 1A-D.

Figure 7A:
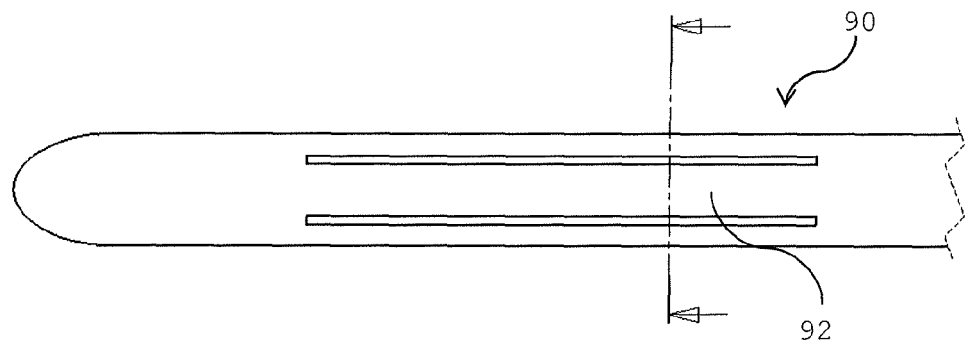
FIGS. 7A-C are schematic illustrations of a malecot catheter for stimulating a portion of a subject's bladder, in accordance with some applications of the present invention.
Figure 7B:
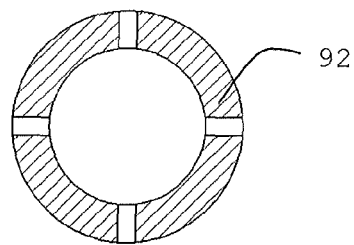
Figure 7C:
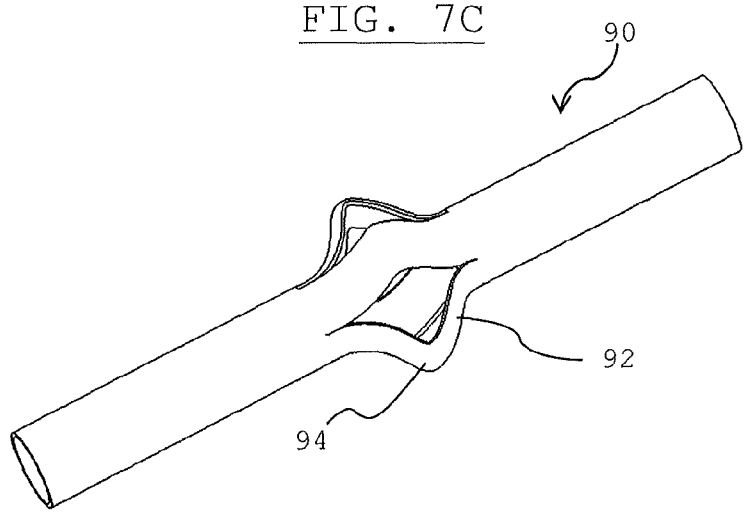

Reference is now made to FIGS. 7A-B, which are schematic illustrations of a malecot catheter 90 for stimulating a portion of a subject's bladder, in accordance with some applications of the present invention. Catheter 90 is inserted into the subject's bladder via the subject's urethra in a contracted state, as shown in FIG. 7A. The distal end of the catheter defines a plurality of radially-extendable elements 92. When the catheter is in the contracted state the radially-extendable elements do not extend from the catheter. When the distal end of catheter 90 is disposed inside the subject's bladder, the radially-extendable elements are extended radially, such that catheter 90 is configured as shown in FIG. 7C.

Typically, when the radially-extendable elements are in extended states, the elements are shaped so as to define angular portions 94. For some applications, the angular portions perform one or more of the functions described hereinabove with reference to protruding members 28. For example, the angular portions may be electrical contacts, which are used to provide electrical stimulation to the subject's bladder. Alternatively or additionally, the angular portions may be used to provide mechanical stimulation to the subject's bladder.

Figure 8A:
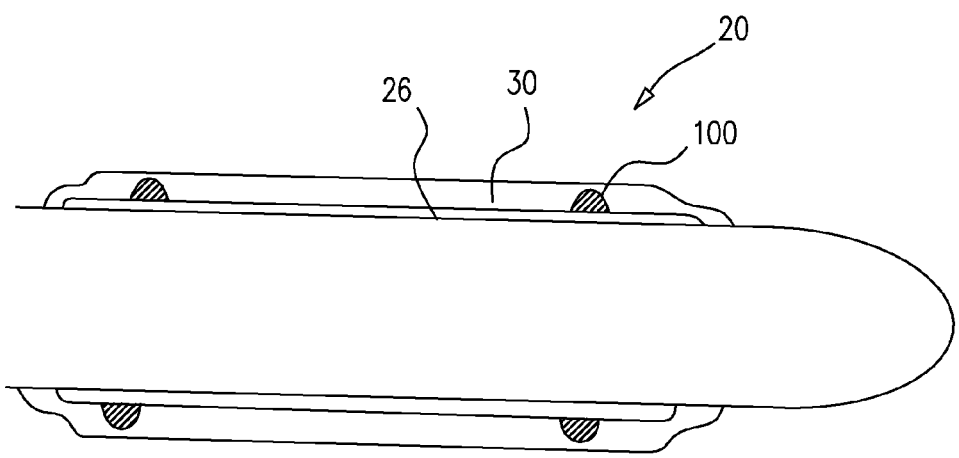
FIGS. 8A-B are schematic illustrations of an outer balloon that is shaped to define protrusions therefrom in an inflated state thereof, in accordance with some applications of the present invention.
Figure 8B:
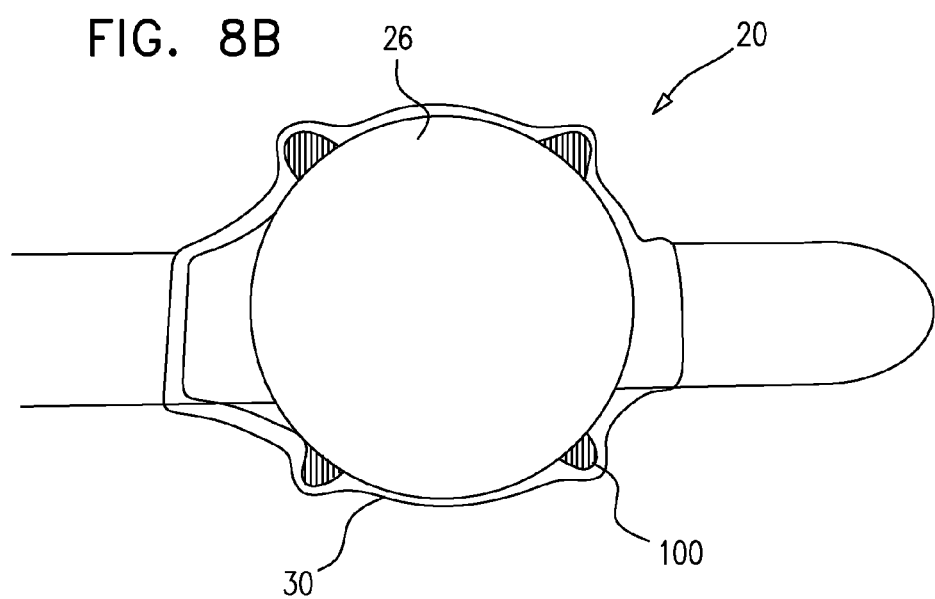

Reference is now made to FIGS. 8A-B, which are schematic illustrations of outer balloon 30, the outer balloon being shaped to define protruding portions 100 therefrom, in an inflated state thereof, in accordance with some applications of the present invention. It is noted that for some applications, inner balloon 26 is configured to define protruding portions 100 therefrom. For such applications, an outer balloon may or may not be used with the inner balloon.

For some applications, when the outer balloon 30 (or inner balloon 26) is molded, portions 100 are formed from a generally similar material to that of the remainder of the balloon, but the material from which portions 100 is formed is less stretchable than the remainder of the balloon. For example, the balloon may be formed from silicone, and the silicone that is used for portions 100 is silicone having a greater durometer than that of the remainder of the balloon. The balloon is typically formed such that in a non-stretched state of the balloon the outer surfaces of portions 100 are flush with the outer surface of the remainder of the balloon, as shown in FIG. 8A. The balloon is inserted into the subject's bladder in the deflated state, such that the protruding portions do not cause discomfort and/or damage to the subject's urethra during insertion therethrough.

When balloon 100 is stretched, e.g., by inner balloon 26 being inflated, the remainder of balloon 100 stretches more than portions 100. Therefore, portions 100 protrude from the portions of the balloon that surround portions 100. Typically, inner balloon 26 is inflated when the balloons are disposed inside the subject's bladder, as described hereinabove.

For some applications, protruding portions 100 from balloon 30 perform one or more of the functions described hereinabove with reference to protruding members 28. For example, the protruding portions may be used to provide mechanical stimulation the subject's bladder (e.g., the trigone area and/or a different area of the subject's bladder). For some applications, balloon 30 is used for inserting into a portion of the subject's body other than the bladder, and/or inserting into the subject's body via a bodily lumen of the subject, or a different portion of the subject's body, other than the urethra, e.g., as described hereinabove.

For some applications, balloon 26 comprises more than two, and/or less than twenty non-contiguous protruding portions. Each of the protruding portions is typically separated from an adjacent protruding portion by a distance of at least 1 mm.

For some applications, a balloon is used to stimulate the bladder, the balloon comprising portions thereof that have respective characteristics. The balloon is configured such that in an inflated state of the balloon, the balloon defines a non-uniform outer surface. For example, the balloon may be configured to assume a ridged outer surface or a waved outer surface, in an inflated state thereof. Typically, for such applications, the balloon is molded such that respective portions of the balloon are made of respective materials, and/or the respective portions are made of the same material, the material having respective levels of flexibility and/or hardness. For some applications, the outer surface of the balloon is abrasive, in order to facilitate mechanical stimulation of the bladder by the outer surface.

Figure 9A:
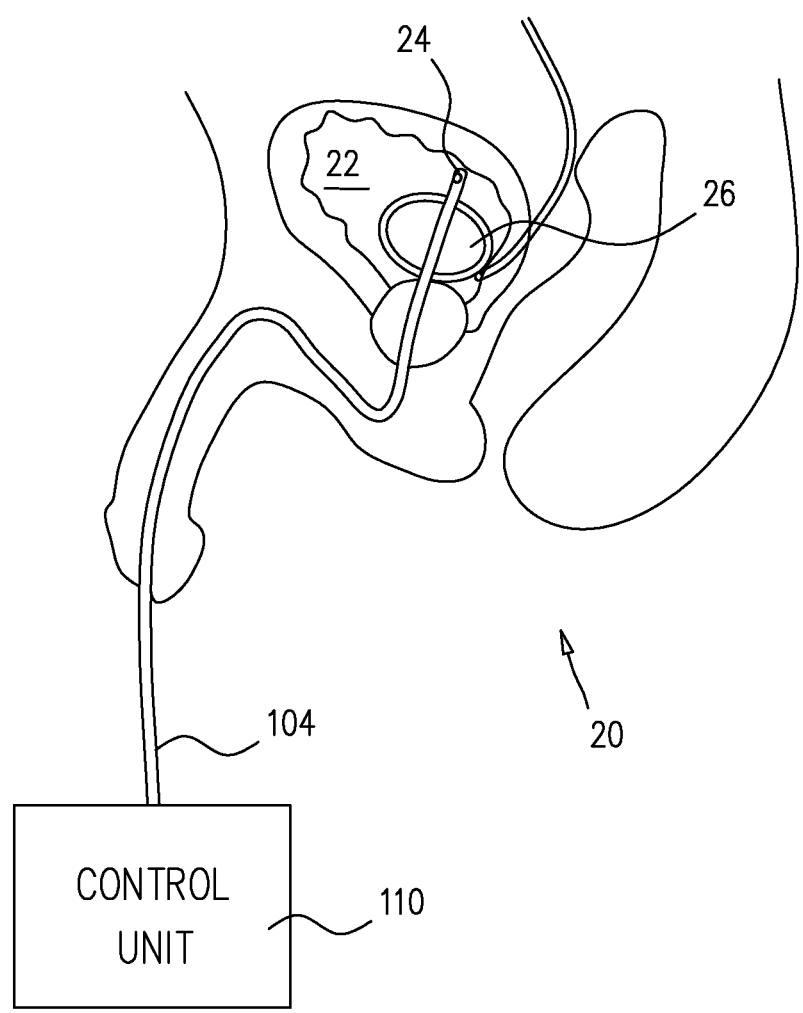
FIGS. 9A-C are schematic illustrations of a catheter that facilitates mechanical stimulation of the subject's bladder, in accordance with some applications of the present invention.
Figure 9B:
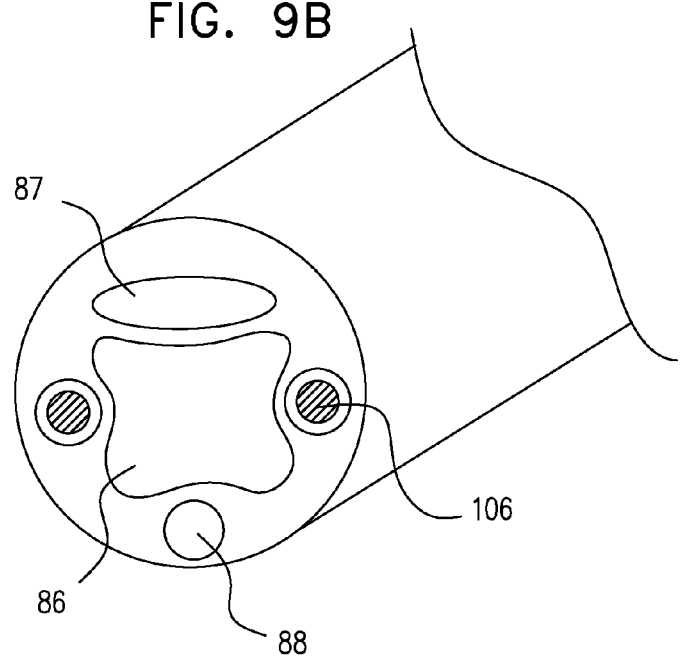
Figure 9C:
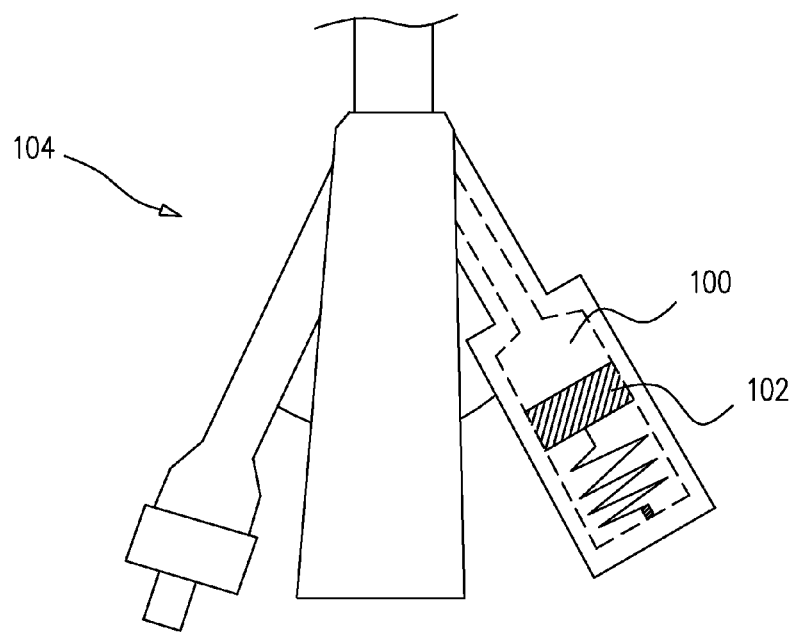

Reference is now made to FIGS. 9A-C which are schematic illustrations of catheter 20, the catheter being configured to facilitate stimulation of the subject's bladder, in accordance with some applications of the present invention. As shown in FIG. 9A, a control unit 110 is disposed outside the subject's body. For some applications, the control unit drives an electrical current into the inner wall of bladder 22, as described hereinabove. Alternatively or additionally, the control unit facilitates mechanical stimulation of the subject's bladder. For some applications, the subject's bladder is mechanically stimulated by catheter 20 in the absence of a control unit, in accordance with the techniques described hereinbelow. For some applications, protruding members 28 protrude from balloon 26, which is disposed at the distal end of catheter, the protruding members being configured to facilitate electrical and/or mechanical stimulation of the bladder, as described hereinabove. Alternatively or additionally, a balloon at the distal end of the catheter is configured to define protruding portions 100, the protruding portions being configured to facilitate mechanical stimulation of the bladder, as described with reference to FIGS. 8A-B.

For some applications, catheter 20 is used to apply stimulation (e.g., electrical or mechanical stimulation) to the trigone area of the subject's bladder. Alternatively, catheter 20 is used to apply stimulation (e.g., electrical or mechanical stimulation) to a different area of the subject's bladder. For some applications, catheter 20 is placed against the bladder wall and used to stimulate the bladder wall irrespective of the location of catheter 20 with respect to the bladder wall.

For some applications, control unit 110 facilitates mechanical stimulation of the subject's bladder by controlling the level of inflation of balloon 26, which is disposed at the distal end of the bladder. In accordance with respective applications, the volume of the balloon is varied with time in accordance with a sinusoidal wave pattern, a square wave pattern, a trapezoidal wave pattern, and/or another wave pattern. For some applications, the frequency with which the volume of the balloon is modulated is more than 0.1 Hz, and/or less than 1 Hz. Alternatively, the frequency with which the volume of the balloon is modulated is less than 0.1 Hz (e.g., less frequently than once an hour). Typically, even when the volume of the balloon is being modulated, the volume of the balloon does not fall below 5 cc, and the diameter of the balloon does not fall below 1 cm. As described hereinabove, for some applications, balloon 26 is inflated to a maximum volume of more than 30 cc, e.g., more than 50 cc, more than 100 cc, or more than 250 cc.

For some applications, when modulating the volume of the balloon, the control unit accounts for fluid that leaks from the balloon, such that the maximum volume of the balloon remains constant. For some applications, the control unit electrically stimulates the bladder when balloon 26 is maximally inflated, and/or otherwise coordinates electrical and mechanical stimulation cycles. Alternatively, the control unit provides electrical and mechanical stimulation, the electrical and mechanical stimulation not being coordinated with one another.

For some applications, a reservoir 100 of inflation fluid (e.g., saline, or air) is disposed outside the subject's body (e.g., in the vicinity of the control unit). The control unit controls a transfer of fluid from the external reservoir to balloon 26, for example, using a piston 102 at proximal end 104 of the catheter (FIG. 9C), a pump disposed within catheter 20, a peristaltic pump, and/or a different sort of pump. For some applications, a level of inflation of balloon 26 is controlled manually, for example, via a manually-controlled pump disposed outside the subject's body (e.g. in the vicinity of the control unit). For some applications, the balloon is inflated using ambient air.

As described hereinabove, and as shown in FIG. 9B, typically the shaft of catheter 20 defines urine-drainage lumen 86 to facilitate outflow of urine from the subject's bladder. For some application, lumen 86 is blocked periodically, in order to allow the bladder to fill with urine, thereby mechanically stimulating the bladder by causing the bladder wall to be stretched.

For some applications, control unit 110 facilitates mechanical stimulation of the subject's bladder by vibrating a portion of catheter 20. For some applications, the control unit vibrates a distal portion of the catheter (e.g., balloon 26). For example, wires 106 (FIG. 9B) may be disposed in the shaft of catheter 20 and coupled to balloon 26 and control unit 110 at respective ends of the wires. The control unit vibrates balloon 26 by controlling movement of the wires. Alternatively, a pendulum (not shown) may be disposed inside the balloon and the balloon is vibrated by the pendulum moving (e.g., by the pendulum passively moving due to movement of the subject, or by the pendulum being actively moved by the control unit). For some applications, a pendulum disposed inside balloon 26 is left inside the bladder in the absence of catheter 20.

For some applications, the control unit vibrates the shaft of the catheter. For some applications, control unit vibrates balloon 26 and/or a different portion of catheter 20 by directing ultrasound waves toward the catheter, e.g., toward the catheter shaft.

For some applications, a device is placed inside bladder 22 and remains inside the subject's bladder, in the absence of a catheter, in order to provide mechanical stimulation to the subject's bladder. For example, an expandable structure (e.g., a balloon) may be inserted into the subject's bladder (e.g., via a catheter) and left inside the subject's bladder, in the absence of a catheter, for more than one hour, e.g., for more than one day. Alternatively, a non-expandable structure, for example, a hard structure (such as a ball), may be inserted into the subject's bladder (e.g., via a catheter) and left inside the subject's bladder, in the absence of a catheter, for more than one hour, e.g., for more than one day. The expandable or non-expandable structure provides mechanical stimulation to the subject's bladder by passively moving inside the bladder.

For some applications, the expandable or non-expandable structure is biodegradable and is left inside the subject's bladder to biodegrade. Alternatively, subsequent to being placed in the bladder and being left in the bladder for a given period of time, the structure is removed from the subject's bladder, e.g., via a catheter, and/or using a different extraction device (such as a thread that is coupled to the structure).

For some applications, bladder 22 and/or a device that is placed inside the bladder is vibrated using an extracorporeal device. For example, sonic or ultrasonic waves may be directed toward the bladder and/or toward a device disposed inside the bladder. For some applications, sonic or ultrasonic waves are directed toward the bladder from a location (e.g., a suprapubic location) outside the subject's body, in order to mechanically stimulate the bladder by vibrating the bladder. Alternatively or additionally, the sonic or ultrasonic waves are directed toward the bladder in order to stimulate the bladder by heating tissue of the bladder.

Alternatively or additionally, a metallic device (e.g., a catheter having a metallic tip, or a metallic ball) is placed inside the subject's bladder and is vibrated by directing a magnetic field toward the subject's bladder from a location (e.g., a suprapubic location) outside the subject's body.

For some applications, mechanical stimulation is applied to the subject's bladder from a location of the subject's body that is outside of the subject's bladder. For example, a location within the subject's vagina or anus may be vibrated in order to provide mechanical stimulation to the subject's bladder.

For some applications, balloon 26 is placed inside the subject's bladder, the balloon being disposed at the distal end of catheter 20, as shown in FIG. 9A. The subject's bladder is mechanically simulated by pushing and/or pulling the balloon and/or the catheter shaft. For example, the catheter shaft may be pulled (manually, or by control unit 110). Alternatively or additionally, the catheter shaft may be pushed distally (manually, or by control unit 110), such that balloon 26 is pushed against the distal wall of the bladder. For some applications, control unit 110 varies the length of the catheter shaft, for example, by varying the length of wires 106 (which are disposed inside the shaft), thereby causing balloon 26 and/or protrusions therefrom to rub against the wall of bladder 22.

For some applications, a parameter of the subject's body, e.g., a parameter of the subject's urine, such as urine flow rate, or urine impedance is measured. For example, electrodes disposed on catheter 20 may be configured to detect the impedance of the subject's urine. For some applications, urine impedance is interpreted by the control unit as being indicative of urine osmolarity, since urine impedance is typically correlated with urine osmolarity. For some applications, urine impedance is interpreted by the control unit as being indicative of urine flow, since urine impedance is typically correlated with urine osmolarity, and, in turn, urine osmolarity is typically correlated with urine flow.

Responsively to the measured parameter, control unit 110 controls a parameter of a stimulation that is applied to the subject's bladder. For example, the control unit may vary a parameter of an electrical current that is applied to the subject's bladder. Alternatively or additionally, the control unit may vary a parameter of mechanical stimulation that is applied to the subject's bladder (e.g., a frequency with which the volume of balloon 26 is modulated, a frequency with which catheter 20 is vibrated, and/or a different parameter).

For some applications, closed loop feedback techniques as described in PCT Application Publication WO 10/067360 to Bar-Yoseph, which is incorporated herein by reference, may be used in conjunction with techniques for stimulating the bladder that are described herein. For example, the stimulation may be provided responsively to an input from at least one internal or external sensor that generates an indication of a body function, and/or responsively to an input from another device, such as a pacemaker or a urine analysis system. Alternatively or additionally, input may be provided by a user, e.g., in response to a subjective feeling.

For some applications, the sensor includes a sensor that senses a urinary parameter, such as urine chemistry, urine volume, and/or urine flow. Alternatively or additionally, the sensor includes a sensor that senses a parameter related to kidney function, such as GFR, urine flow, urine composition, secretion of hormones from the kidney (in blood and/or urine), creatinine levels, and/or insulin levels. Further alternatively or additionally, the sensor includes a sensor that senses a function of the urinary system, for example, urinary parameters, peristalsis, and/or pressure. Still further alternatively or additionally, the sensor includes a physiological sensor for measuring non-urinary parameters of the body, for example, blood chemistry, blood pressure, heart rate, breathing rate, lung fluid volume, and/or ECG.

For some applications, stimulation is provided responsively to an input from the subject and/or a healthcare professional. For some applications, stimulation is provided responsively to an environmental sensor. For example, an acceleration sensor may be used to detect movement (which may be indicative of blood pressure changes) of the subject, and/or body posture of the subject. For example, the sensor may detect that the subject is supine, which may indicate that the subject is undergoing a rest period, during which cardiac demand is low, relative to cardiac demand during active periods of the subject. Alternatively or additionally, a temperature sensor may be used to detect the ambient temperature, and the bladder stimulation is provided responsively thereto.

Reference is now made to FIGS. 10A-E, which are schematic illustrations of a covering sheath 111 that is placed on inner balloon 26 and that acts as a protrusion-member-protection layer, in accordance with some applications of the present invention. Covering sheath 111 is placed over balloon 26 such that the covering sheath acts a protrusion-member-protection layer, in a generally similar manner to that described hereinabove, for example, with reference to outer balloon 30.

Typically, covering sheath 111 is configured to protect the subject's urethra during insertion of the catheter into the subject's bladder (when balloon 26 is in a deflated state), by the protruding members not protruding from the sheath during the insertion. For example, during the insertion, the covering sheath may at least partially cover the protruding members, or may form a surface that is flush with outer surfaces of the protruding members. For some applications, the covering sheath protects the protruding members from being damaged and/or from becoming decoupled from balloon 26 during insertion of the catheter into the subject's bladder. Typically, when the balloon is disposed inside the subject's bladder, the balloon is inflated. Covering sheath 111 is shaped to define holes 42, through which protruding members 28 protrude when balloon 26 is in an inflated state. For some applications, edges 40 of the covering sheath that define holes 42 are thickened with respect to other portions of the covering sheath. For some applications, the covering sheath covers electrical leads that are coupled to the protruding members.

Figure 10A:
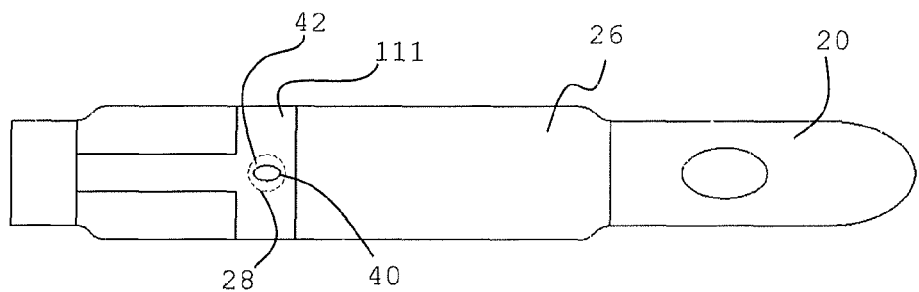
FIGS. 10A-E are schematic illustrations of a covering sheath that is placed on a portion of a balloon, in accordance with some applications of the present invention.
Figure 10B:
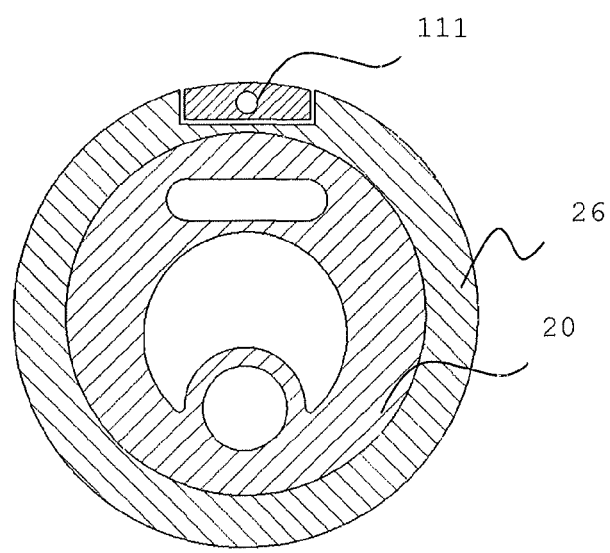

FIG. 10B shows a cross-sectional view of the shaft of catheter 20. Balloon 26 is disposed around a distal portion of the shaft, as described hereinabove. For some applications, the balloon defines a groove that is shaped so as to conform with the shape of sheath 111. Typically, the groove is shaped such that when sheath 111 is placed inside the groove, the outer surfaces of the sheath and the balloon are flush with one another, as shown in FIG. 10B. It is noted that, for some applications, balloon 26 does not define grooves. For example, the covering sheath may be placed on top of the outer surface of the balloon such that the outer surfaces of the sheath and the balloon are not flush with one another (application not shown).

Figure 10C:
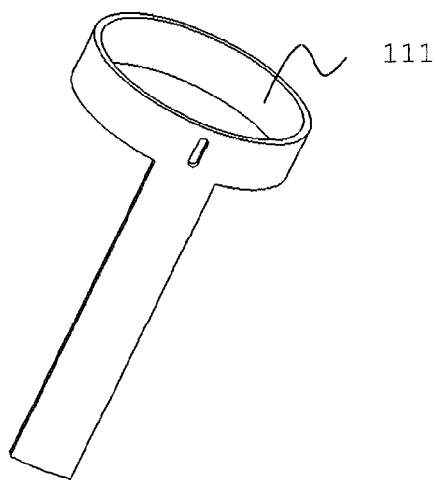

It is noted that although a covering sheath having a specific shape is shown in FIGS. 10A-C, the scope of the present invention includes having a generally similar covering sheath to that described hereinabove, but with the covering sheath having a different shape from the specific shape shown in FIGS. 10A-C. For example, the covering sheath may be shaped as a ring, a belt, a strip, in a serpentine shape, and/or in any other shape.

Figure 10D:
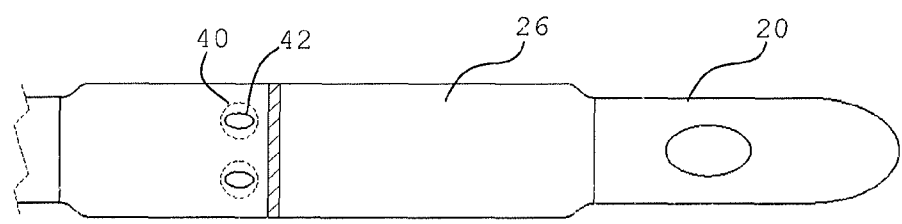
Figure 10E:
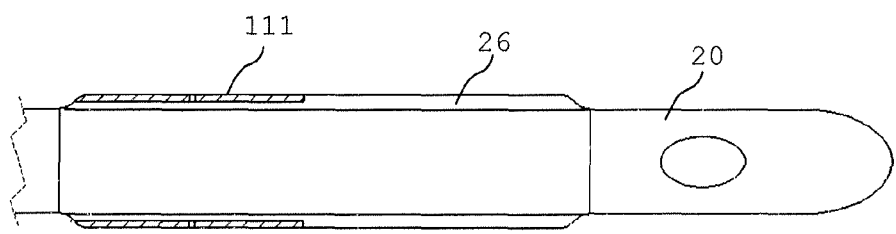

FIGS. 10D-E show covering sheath 111, the covering sheath being shaped so as to cover the entire circumference of a portion of balloon 26. For some applications, balloon 26 is indented so as to conform with the shape of sheath 111. Typically, the indentation in balloon 26 is shaped such that when sheath 111 is placed inside the indentation, the outer surfaces of the sheath and the balloon are flush with one another, as shown in FIG. 10E. It is noted that, for some applications, balloon 26 does not define an indentation. For example, the covering sheath may be placed on top of the outer surface of the balloon such that the outer surfaces of the sheath and the balloon are not flush with one another (application not shown).

For some applications, covering sheath 111 is made of the same material as balloon 26. For example, the covering sheath may comprise a portion of balloon 26 that has been cut from the rest of the balloon. Alternatively, the covering sheath and the balloon may be molded separately, and/or may be made of different materials.

Figure 11A:
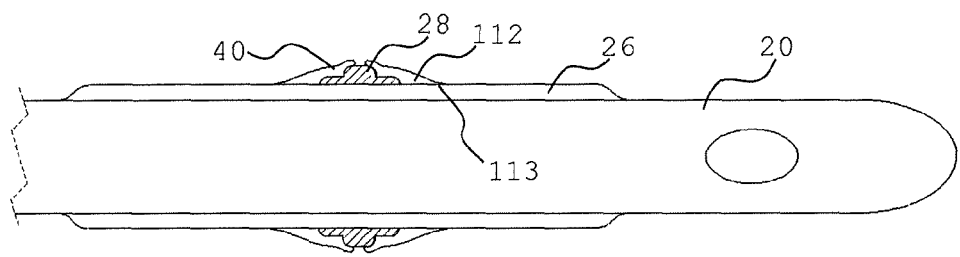
FIGS. 11A-C are schematic illustrations of a patch that is placed on a portion of a balloon, in accordance with some applications of the present invention.
Figure 11B:
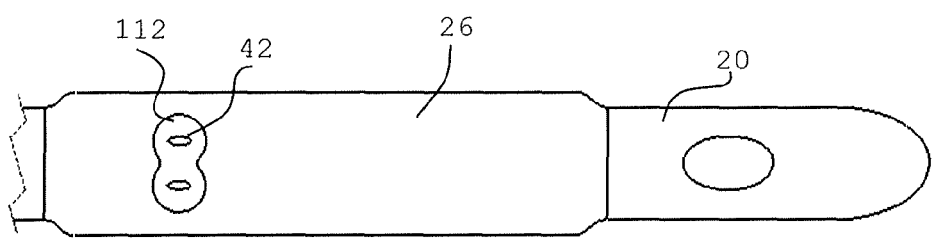
Figure 11C:
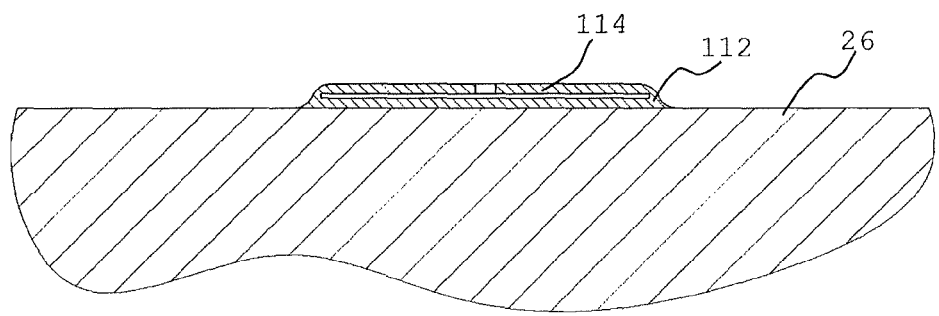

Reference is now made to FIGS. 11A-C, which are schematic illustrations of a patch 112 (e.g., a silicone patch) that is placed on a portion of balloon 26, in accordance with some applications of the present invention. Patch 112 is placed over balloon 26 such that the patch acts a protrusion-member-protection layer, in a generally similar manner to that described hereinabove, for example, with reference to outer balloon 30.

Typically, patch 112 is configured to protect the subject's urethra during insertion of the catheter into the subject's bladder (when balloon 26 is in a deflated state), by the protruding members not protruding from the patch during the insertion. For example, during the insertion, the patch may at least partially cover the protruding members, or may form a surface that is flush with outer surfaces of the protruding members. For some applications, the patch protects the protruding members from being damaged and/or from becoming decoupled from balloon 26 during insertion of the catheter into the subject's bladder.

Typically, when the balloon is disposed inside the subject's bladder, the balloon is inflated. Patch 112 is shaped to define holes 42, through which protruding members 28 protrude when balloon 26 is in an inflated state. For some applications, edges 40 of the patch that define holes 42 are thickened with respect to other portions of the patch. For some applications, the patch covers electrical leads that are coupled to the protruding members.

For some applications, the patch is shaped as a figure-of-eight and is configured to cover two protruding members, as shown in FIG. 11B. However, it is noted that although a patch having a specific shape is shown in FIG. 11B, the scope of the present invention includes having a generally similar patch to that described hereinabove, but with the patch having a different shape from the specific shape shown in FIG. 11B. For example, the patch may be shaped as a ring, a belt, a strip, in a serpentine shape, and/or in any other shape.

For some applications, the thickness of the patch decreases from a central portion of the patch to the edges of the patch. For example, the decrease in the thickness of the patch may be such that the outer surface of the balloon and the outer surface of the patch form a generally smooth interface 113, as shown in FIG. 11A.

FIG. 11C shows a double-layered patch 112 the patch defining a slit 114 between inner and outer layers of the patch, in accordance with some applications of the present invention. For some applications, the slit is open, so as to facilitate insertion of protruding member 28 and or other materials (e.g., adhesive) into the slit. Typically, the protruding member is inserted into the slit, and the outer layer of the patch acts as a protruding-member-protection layer, in a generally similar manner to that described hereinabove.

It is noted that techniques described with reference to FIGS. 10A-E and those described with reference to FIGS. 11A-C may be practiced in combination with each other.

Figure 12A:
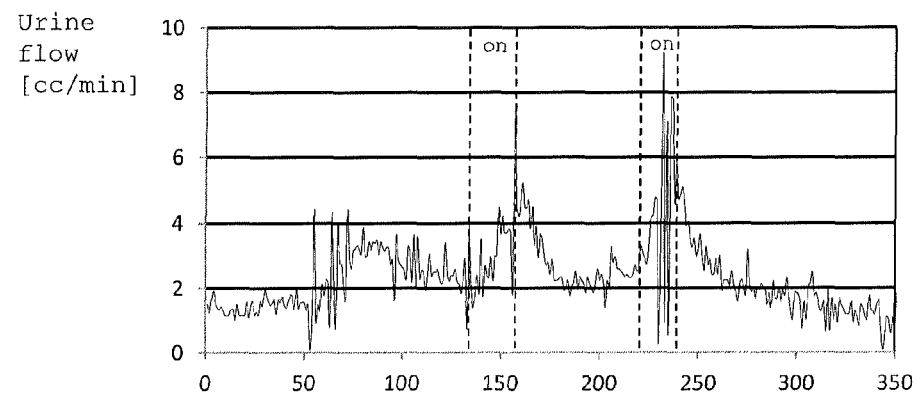
FIGS. 12A-E are graphs showing the results of experiments conducted in accordance with some applications of the present invention.
Figure 12A:
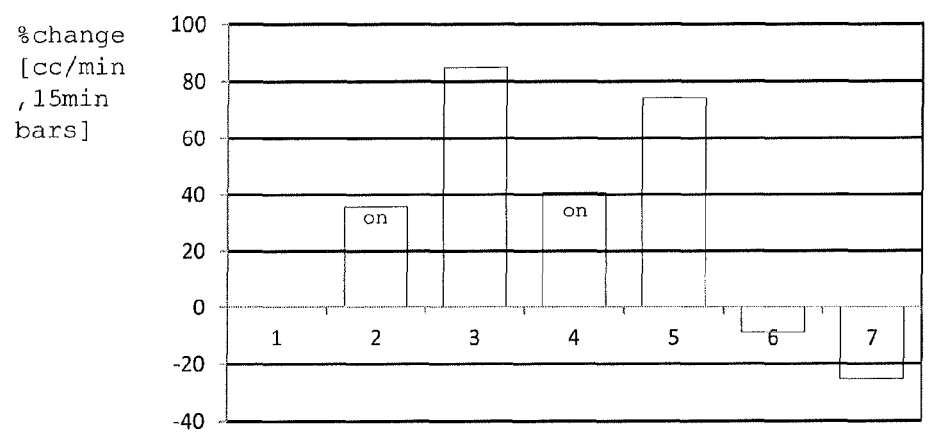
Figure 12A:
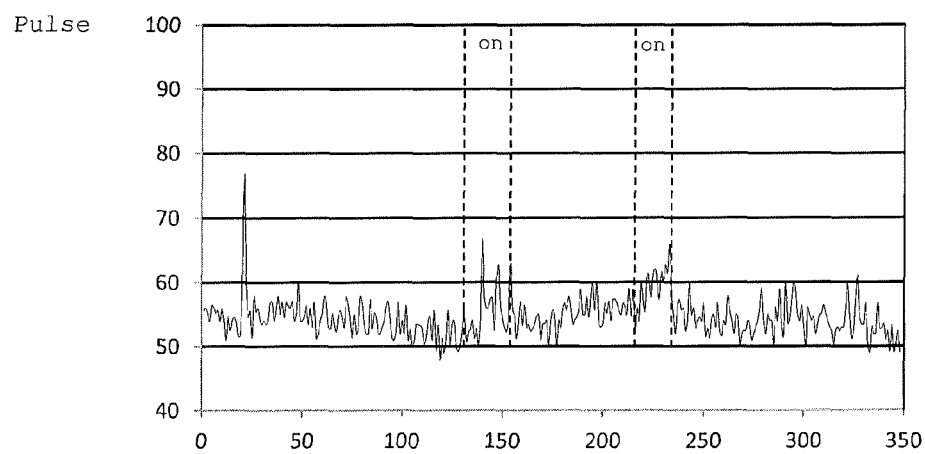

Reference is now made to FIG. 12A, which shows the results of an experiment, conducted in accordance with some applications of the present invention. Electrical stimulation was applied to the trigone area of the bladders of several sheep. The electrical stimulation was applied via two electrical contacts that protruded from a balloon disposed on a distal portion of a catheter, as described hereinabove. The electrical stimulation was applied during stimulation periods lasting 15 minutes each. The stimulation was applied at 100 Hz, and 10 mA, with a 0.7 msec pulse width, and with a biphasic rectangular waveform. The graphs shown in FIG. 12A show the results of the stimulation one of the sheep.

The upper graph of FIG. 12A shows the urine flow [cc/min] that was measured in the sheep. The dashed vertical lines in the upper graph with the word "ON" therebetween, indicate the period during which the stimulation was turned on. It may be observed that for two of the periods in which the stimulation was applied (between approximately 140 min. and 155 min., and between approximately 220 min. and 235 min.), the urine flow increased, and the flow of urine remained elevated for a time period following the stimulation.

The middle graph of FIG. 12A presents the percentage change in average urine flow (a) during the 15 minutes of stimulation versus 15 minutes preceding the stimulation period, and (b) for the 15 minutes following the stimulation period versus the 15 minutes preceding the stimulation period, for each of the stimulation periods. It may be observed that for two of the periods in which the stimulation was applied (between approximately 140 min. and 155 min., and between approximately 220 min. and 235 min.), the urine flow increased, and the flow of urine remained elevated for a time period following the stimulation.

The bottom graph of FIG. 12A shows the pulse of the sheep, as measured during the experiment. It may be observed that the sheep's pulse remained substantially unchanged during the stimulation of the sheep's bladder, indicating that the stimulation did not cause stress to the sheep.

The results shown in FIG. 12A indicate that electrical stimulation of a subject's bladder, in accordance with the techniques described herein may cause an increase in the subject's urine flow, without causing a substantial change to the subject's pulse. It is noted that although electrical stimulation was applied to several sheep, the stimulation did not result in a substantial increase in urine flow in all of the sheep. Nevertheless, the results shown in FIG. 12A indicate that, for at least some subjects, electrical stimulation of the bladder may be effective at increasing urine flow.

Figure 12B:
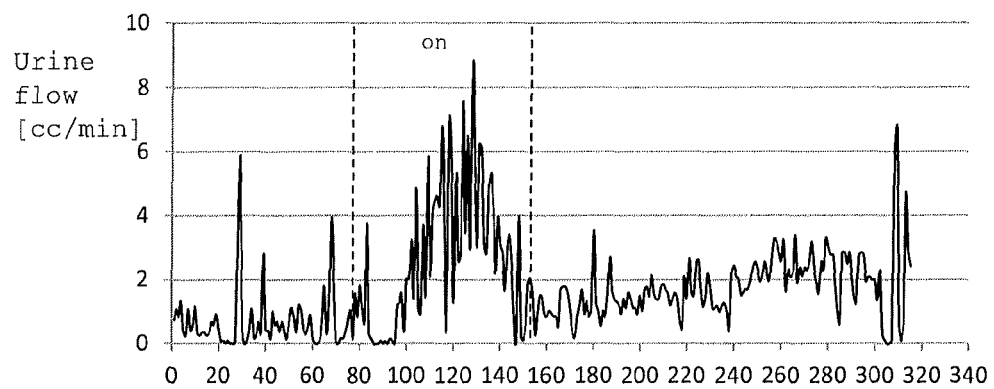
Figure 12B:
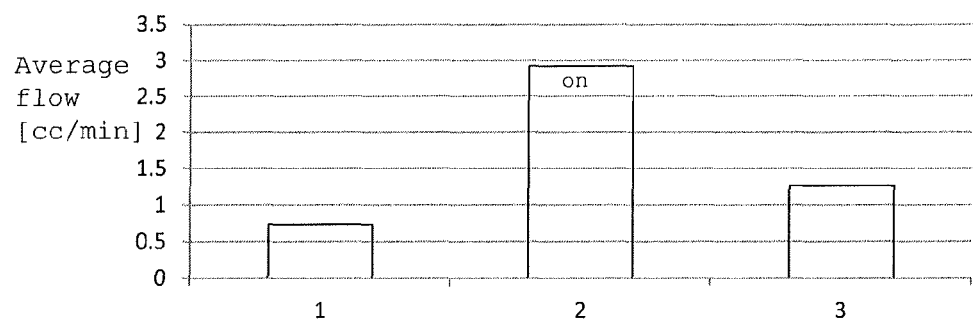
Figure 12B:
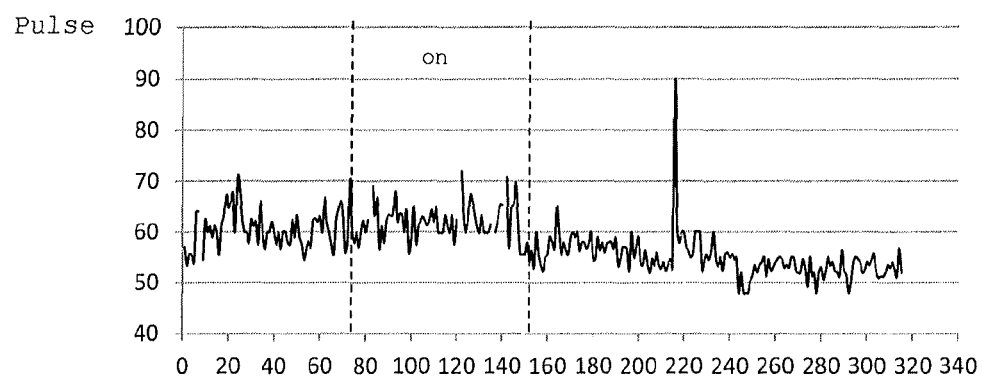

Reference is now made to FIG. 12B, which shows the results of an experiment, conducted in accordance with some applications of the present invention. Mechanical stimulation was applied to several sheep by inserting a distal portion of a catheter into the sheep's bladders. Two protrusions from a balloon at the distal portion of the catheter were oriented toward the trigone area of the sheep's bladders. An 88 gram weight was tied to the proximal end of the catheter for a period of 60 minutes, to facilitate the mechanical stimulation. The graphs shown in FIG. 12B show the results of the stimulation one of the sheep.

The upper graph of FIG. 12B shows the urine flow that was measured in the sheep. The dashed vertical lines in the upper graph with the word "ON" therebetween, indicate the period during which the stimulation was applied. It may be observed that during the stimulation period, the urine flow increased.

The middle graph of FIG. 12B presents the average urine flow rate (a) for a 60 minute period before the stimulation was applied (b) during the 60 minutes of stimulation, and (c) for the 60 minutes following the stimulation period. It may be observed that during the stimulation period, the urine flow increased substantially, and remained somewhat elevated for the period that followed the stimulation period.

The bottom graph of FIG. 12B shows the pulse of the sheep, as measured during the experiment. It may be observed that the sheep's pulse remained substantially unchanged during the stimulation of the sheep's bladder, indicating that the stimulation did not cause stress to the sheep.

The results shown in FIG. 12B indicate that mechanical stimulation of a subject's bladder, in accordance with the techniques described herein may cause an increase in the subject's urine flow, without causing a substantial change to the subject's pulse. It is noted that although mechanical stimulation was applied to several sheep, the mechanical stimulation did not result in a substantial increase in urine flow in all of the sheep. Nevertheless, the results shown in FIG. 12B indicate that, for at least some subjects, mechanical stimulation of the bladder may be effective at increasing urine flow.

Figure 12C:
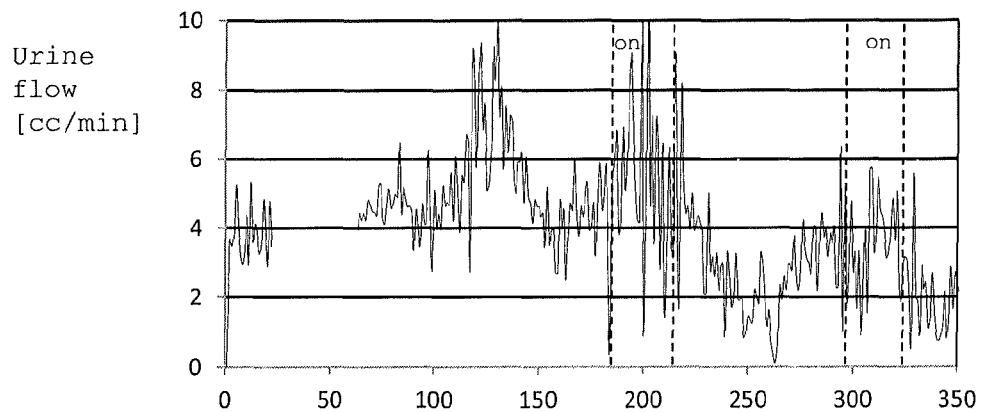
Figure 12C:
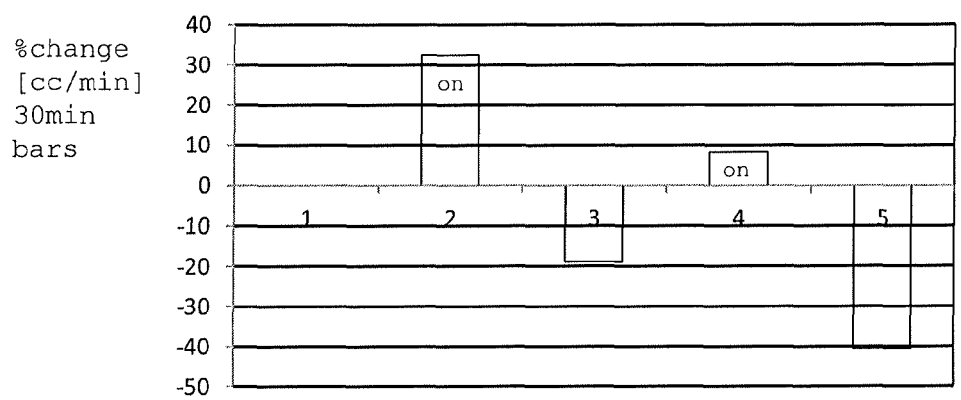
Figure 12C:
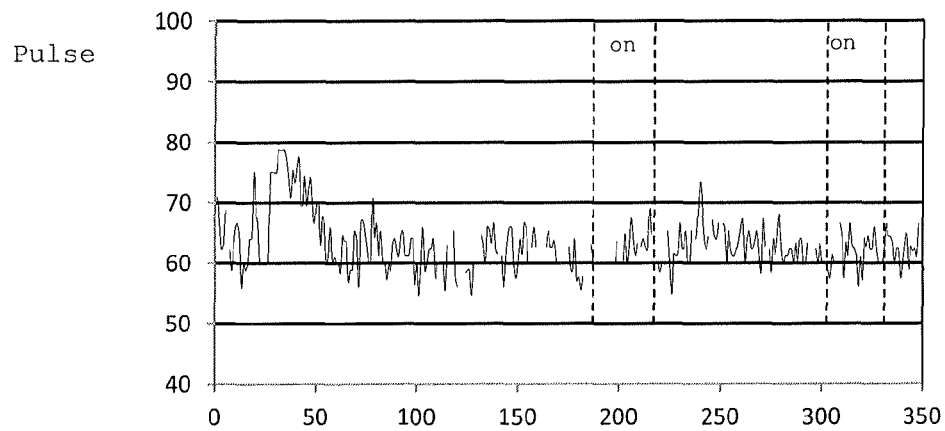

Reference is now made to FIG. 12C, which shows the results of an experiment conducted in accordance with some applications of the present invention. Mechanical stimulation was applied to several sheep by inserting a distal portion of a catheter into the sheep's bladders. Two protrusions from a balloon at the distal portion of the catheter were oriented toward the trigone area of the sheep's bladders. During stimulation periods lasting 30 minutes each, the volume of the balloon was modulated between 20 cc and 40 cc, the modulation cycle being repeated two to three times a minute.

The upper graph of FIG. 12C shows the urine flow that was measured in the sheep. The dashed vertical lines in the upper graph with the word "ON" therebetween, indicate the period during which the stimulation was applied. It may be observed that during the stimulation periods, the urine flow increased.

The middle graph of FIG. 12C presents the percentage change in average urine flow (a) during the 30 minutes of stimulation versus 30 minutes preceding the stimulation period, and (b) for the 30 minutes following the stimulation versus the 30 minutes preceding the stimulation period, for each of the stimulation periods. It may be observed that for both of the periods in which the stimulation was applied, the urine flow increased.

The bottom graph of FIG. 12C shows the pulse of the sheep, as measured during the experiment. It may be observed that the sheep's pulse remained substantially unchanged during the stimulation of the sheep's bladder, indicating that the stimulation did not cause stress to the sheep.

The results shown in FIG. 12C indicate that mechanical stimulation of a subject's bladder, in accordance with the techniques described herein (e.g., by modulating the volume of a balloon that is placed inside the bladder) may cause an increase in the subject's urine flow, without causing a substantial change to the subject's pulse. It is noted that although mechanical stimulation was applied to several sheep, the mechanical stimulation did not result in a substantial increase in urine flow in all the sheep. Nevertheless, the results shown in FIG. 12C indicate that, for at least some subjects, mechanical stimulation of the bladder may be effective at increasing urine flow.

Figure 12D:
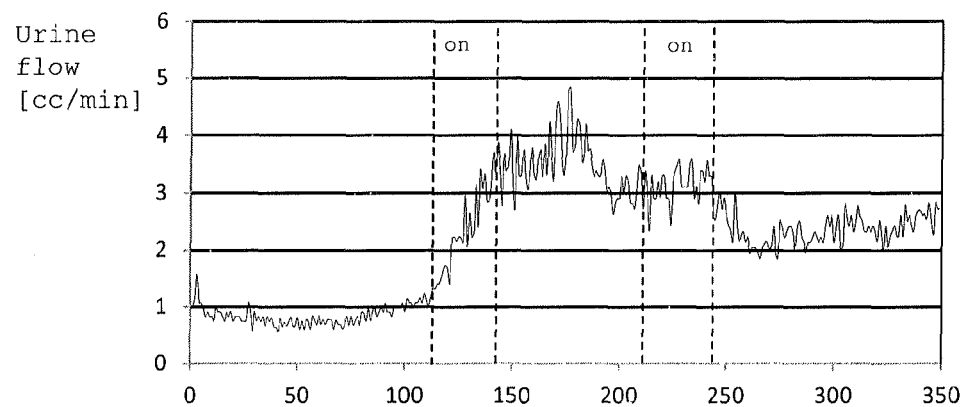
Figure 12D:
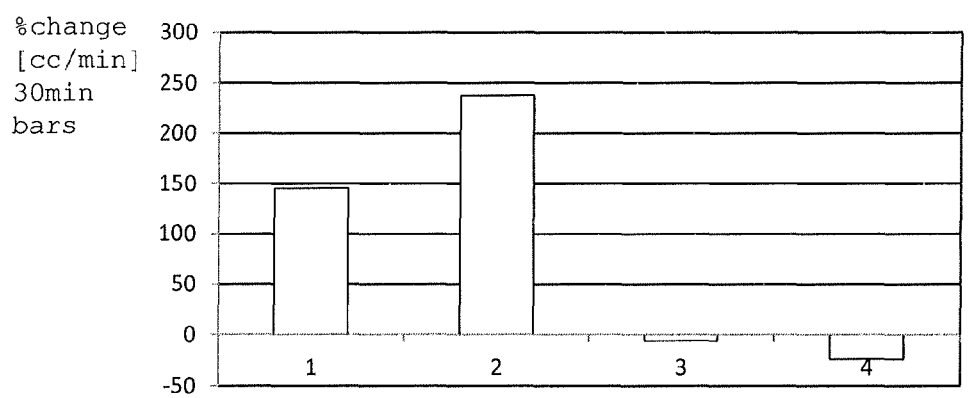
Figure 12D:
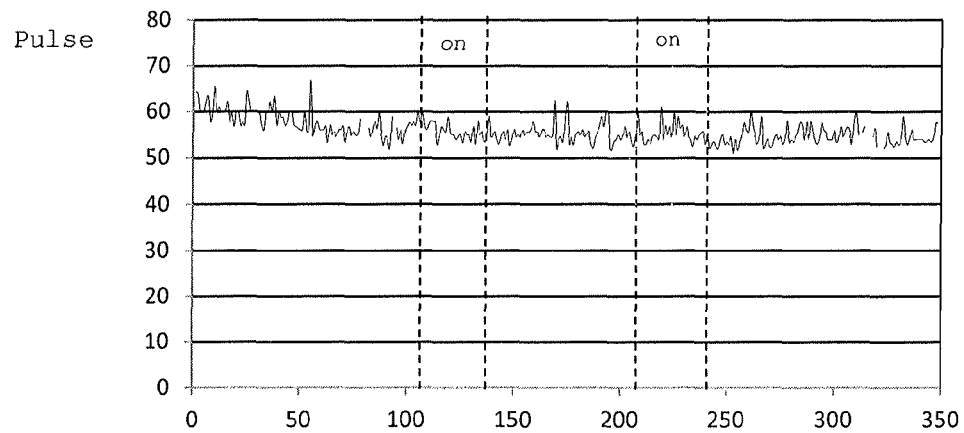

Reference is now made to FIG. 12D, which shows the results of an experiment conducted in accordance with some applications of the present invention. Mechanical stimulation was applied to several sheep by inserting a distal portion of a catheter into the sheep's bladders. Two protrusions from a balloon at the distal portion of the catheter were oriented toward the trigone area of the sheep's bladders. During stimulation periods lasting 30 minutes each, an 88 gram weight was tied to the proximal end of the catheter, to facilitate the mechanical stimulation. During the stimulation periods, the volume of the balloon was modulated between 20 cc and 40 cc, the modulation cycle being repeated two to three times a minute. The graphs shown in FIG. 12D show the results of the stimulation one of the sheep.

The upper graph of FIG. 12D shows the urine flow that was measured in the sheep. The dashed vertical lines in the upper graph with the word "ON" therebetween, indicate the period during which the stimulation was applied. It may be observed that, during the first stimulation period, the urine flow increased. The urine flow remained elevated until after the second stimulation period, there having been an interval of more than 50 minutes between the first and second stimulation periods.

The middle graph of FIG. 12D presents the percentage change in average urine flow (a) during the 30 minutes of stimulation versus 30 minutes preceding the stimulation period, and (b) for the 30 minutes following the stimulation versus the 30 minutes preceding the stimulation period, for each of the stimulation periods. It may be observed that during the first stimulation period the urine flow increased. The urine flow continued to increase subsequent to the first stimulation period. The urine flow decreased slightly during the second stimulation period, and decreased more during the period following the second stimulation period.

The bottom graph of FIG. 12D shows the pulse of the sheep, as measured during the experiment. It may be observed that the sheep's pulse remained substantially unchanged during the stimulation of the sheep's bladder, indicating that the stimulation did not cause stress to the sheep.

The results shown in FIG. 12D indicate that mechanical stimulation of a subject's bladder, in accordance with the techniques described herein (e.g., by modulating the volume of a balloon that is placed inside the bladder) may cause an increase in the subject's urine flow, without causing a substantial change to the subject's pulse. It is noted that although mechanical stimulation was applied to several sheep, the mechanical stimulation did not result in a substantial increase in urine flow in all the sheep. Nevertheless, the results shown in FIG. 12D indicate that, for at least some subjects, mechanical stimulation of the bladder may be effective at increasing urine flow.

Figure 12E:
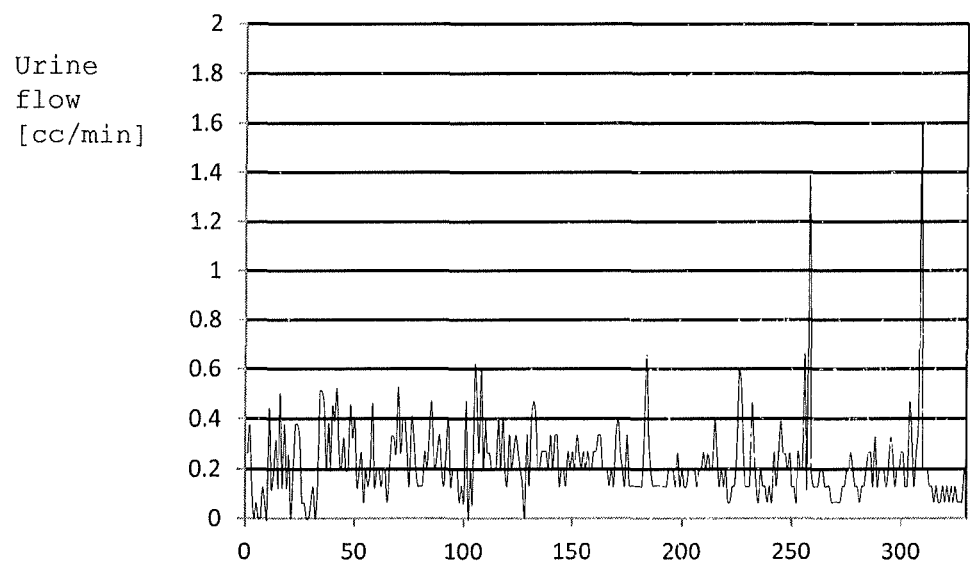
Figure 12E:
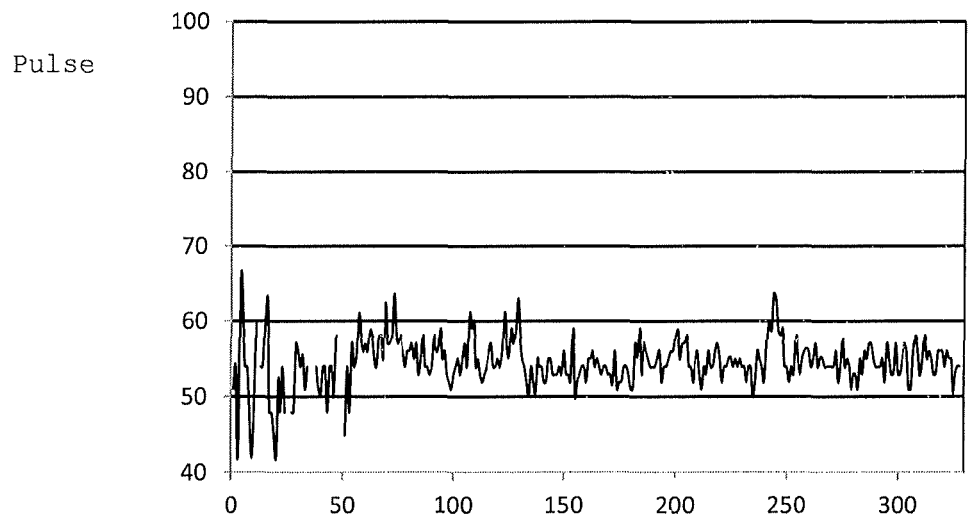

Reference is now made to FIG. 12E, which shows the results of a control experiment, conducted in accordance with some applications of the present invention. A distal portion of a catheter was inserted into a sheep's bladders. Two protrusions from a balloon at the distal portion of the catheter were oriented toward the trigone area of the sheep's bladders. Electrical stimulation was not provided to the bladder via the contacts, the volume of the balloon was not modulated, and a weight was not placed on the catheter.

The upper graph of FIG. 12E shows the urine flow that was measured in the sheep over a period of more than 300 minutes during which the catheter was inserted into the sheep's bladder. The lower graph shows the pulse of the sheep, as measured during the experiment. It may be observed that sheep's urine flow and pulse remained substantially unchanged during the experiment. These results indicate that, for at least some subjects, it may be desirable to apply electrical stimulation to the bladder via the protrusions from the balloon, and/or to move the protrusions, or cause the protrusions to move with respect to the inner bladder wall, in order to cause an increase in urine flow. Alternatively, for some subjects, placing a catheter inside the bladder, a balloon being disposed at the distal end of the catheter, and the balloon defining protrusions therefrom, as described herein, even without applying electrical stimulation to the bladder via the protrusions from the balloon, and/or moving the protrusions, or causing the protrusions to move with respect to the inner bladder wall, may cause an increase in urine flow.

For some applications, the techniques described herein are combined with techniques described in PCT Application Publication WO 10/067360 to Bar-Yoseph and/or in U.S. Provisional Patent Application 61/355,522, filed Jun. 16, 2010, both of which applications are incorporated herein by reference.

For example, for some applications, apparatus and methods are provided for controlling body functions using stimulation of the urinary system. Typically, the body functions include kidney functions such as glomerular filtration rate (GFR), urine flow rate, urine composition, urine density and renal hormone secretion. Optionally or alternatively, the body functions include cardiovascular functions, such as blood pressure, portal pressure, pulmonary pressure, organ (including renal) blood flow, cardiac output, heart rate, intravascular and extravascular fluid volume, pulmonary and body edema levels. Optionally or alternatively, the functions are bodywide systems such as blood chemistry or sympathetic nerve activity.

For some applications, body functions are affected by modifying kidney function. For example, kidney function is modified by controlling a renal reflex, such as, the reno-renal reflex, or the vesico-vascular reflex. Optionally, kidney function is modified by changing a parameter of peristalsis (e.g., by overpacing, with sensing of self-pacing, or at an enforced frequency) of one or both ureters. For some applications, such stimulation modulates a reno-renal reflex mediated by the ureter, and/or affects urine pressure in the kidney.

For some applications, the parts of the urinary system stimulated are parts which are adapted to carry urine, such as the kidney pelvis, the ureter and/or the bladder. Optionally, the stimulated part includes afferent nerves which are affected by the stimulation. Optionally, stimulation in accordance with applications of the present invention is provided in conjunction with other treatment, such as administration of medication and/or stimulation of other parts of the body. For some applications, the treatment(s) control, compensate for, force, manage, modulate and/or stand-in for natural body feedback cycles, e.g., damaged and/or healthy natural body feedback cycles. Optionally, the stimulation and/or control of body physiology are used as a long term treatment, optionally, with a goal of treating, preventing degradation and/or maintaining a state of a patient.

Some applications of the invention are based on experimental data obtained by the inventors that indicates that stimulation of the urinary system can affect kidney function and/or other bodywide functions, rather than merely affecting local function such as peristalsis or bladder voiding. In particular, the inventors obtained experimental data that indicates that stimulating the bladder, bladder trigone, the ureters, as well as other parts of the urinary system, affects kidney and/or other body functions, including functions not directly related to urinary functioning, such as, cardiovascular functions (for example, blood pressure). While not limiting the scope of the present invention, the inventors hypothesize that such stimulation affects existing feedback cycles in the body, possibly by affecting the source of feedback signals (e.g., the afferent nerves), and/or by causing activity of the stimulated portions, which then modulates existing reflex feedback cycles.

In accordance with respective applications of the invention, the stimulation that is provided includes electrical stimulation, chemical stimulation, thermal stimulation and/or mechanical stimulation.

For some applications, an implanted device is used for stimulating the urinary system. Alternatively or additionally, the device includes a transurethrally or transcutaneously inserted stimulator, which may, optionally, extend out of the urethra to an external stimulator controller and/or power source. Optionally, the device includes a stimulator inside the bladder, inside the kidney and/or inside the ureter. Optionally, the device operates by expanding the ureter.

For some applications of the invention, an intraureteral stimulator is provided that is thin and/or soft enough such that the stimulator allows urine flow past the stimulator and/or does not interfere with valves of the urinary tract. Optionally, the stimulator is equipped with an anchoring mechanism, such as, a curved element at an end of the stimulator. For example, a pig tail may be provided on one or both sides of the stimulator. Alternatively or additionally, the stimulator may define a widening form (for example, radially extending arms or a conical coil), which lodges in the urinary system, for example, in the kidney pelvis and/or bladder. For some applications, the stimulator is configured to stimulate the urinary system at the widening form.

Some applications of the present invention relate to treating, modifying, and/or maintaining body functions using a urinary system stimulator device (or system). While in some applications of the invention a device may apply an open loop treatment (whereby a therapy is set for a desired effect), for alternative applications of the invention, the device is configured to receive an input. For example, the device may be configured to receive an input from an internal or external sensor (or more than one sensor), which generates an indication of body function, or to receive an input from other devices (such as a pacemaker or urine analysis system) and/or input from a user (e.g., in response to a subjective feeling of the user). Optionally or alternatively, the stimulation device is used in a manner in which a closed feedback loop is applied.

In some applications of the invention, the sensor includes a sensor of kidney function and urinary parameters, such as one or more of urine chemistry, urine volume and urine flow. Optionally or alternatively, the sensor includes a sensor that senses a parameter associated with kidney function, for example, GFR, urine flow, urine composition, secretion of hormones from the kidney (in blood and/or urine), creatinine levels, and/or insulin levels. Optionally or alternatively, the sensor includes a sensor that senses a parameter associated with urinary systems function, for example, urinary parameters, peristalsis and/or pressure. Optionally or alternatively, the sensor includes a physiological a sensor that senses a parameter associated with non-urinary systems, for example, blood chemistry, blood pressure, heart rate, breathing rate, lung fluid volume and/or ECG. Optionally or alternatively, the sensor includes an input for user entry of a command or of a physiological parameter. Optionally or alternatively to a physiological sensor, an environmental sensor is used. For example, an acceleration sensor may be used to sense movement (which may be indicative of blood pressure changes, for example) or body posture (which may be indicative of the subject undergoing a rest period (e.g., if the subject is supine), during which cardiac demand is lower. Alternatively or additionally, a temperature sensor may be used to indicate environmental temperature (which may be indicative of sweating rate, for example).

Some applications of the invention relate to non-electrical stimulation of the urinary system, for example, thermal, mechanical and/or chemical stimulation of the ureter, trigone and/or kidney. For some applications, a device for mechanical stimulation includes an element which expands inside the ureter and thereby simulates a blockage. Optionally, the element does not block urine flow. Alternatively, the element does block urine flow.

Some applications of the invention relate to an integrated bladder dwelling stimulation system. Optionally, the system is adapted to be inserted through a urethra. Optionally or alternatively, the system is adapted to be inserted via the pubic area. Optionally, the system includes, in a single unit, sensing, control and power functionalities. Optionally, the system is designed to specifically stimulate the trigone.

For some applications, mechanical receptors are triggered by stretching, pressure or vibration. For example, expanding an object in a ureter can simulate blockage of the ureter by a reno-renal reflex. Such expansion, need not block the ureter, but can be used to selectively reduce output from the partially-blocked kidney and/or increase output from an opposite kidney.

For some applications, mechanical stimulation in the ureter is provided intermittently, since chronic dilatation of the ureter may result in refractoriness, with the ureter possibly expanding to a larger volume.

Optionally, the ureter is expanded by a balloon. Optionally or alternatively, the trigone is mechanically activated by one or both of a balloon and/or a stiff mechanical element that is moved by an external or an internal engine or by magnetism.

It is noted with respect to FIGS. 1A-9C that, for some applications, two or more of the following techniques are used in conjunction with each other:

techniques for protecting protruding members 28 (e.g., using a protruding-member-protection layer) described, for example, with reference to FIGS. 1A-3C, 6A-8B, and 10A-11C;

techniques for coupling protruding members 28 to a balloon (or another expandable structure) described, for example, with reference to FIGS. 4A-8B; and techniques for stimulating a subject's bladder described, for example, with reference to FIGS. 9A-C.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   identifying a subject as suffering from an impaired body system, the body system being selected from the group consisting of: a cardiovascular system and a renal system; and
   in response thereto, treating the impaired body system of the subject, by mechanically stimulating a bladder of the subject with a structure.

2. The method according to claim 1, wherein mechanically stimulating the bladder with the structure comprises mechanically stimulating the bladder with a balloon.

3. The method according to claim 1, wherein mechanically stimulating the bladder with the structure comprises mechanically stimulating the bladder with a stiff mechanical element.

4. The method according to claim 1, wherein mechanically stimulating the bladder with the structure comprises moving the structure using an engine.

5. The method according to claim 1, wherein mechanically stimulating the bladder with the structure comprises moving the structure magnetically.

6. The method according to claim 1, wherein mechanically stimulating the bladder comprises controlling a kidney function of the subject selected from the group consisting of: glomerular filtration rate, rate of urine flow from the kidney, urine composition, urine density and renal hormone secretion.

7. The method according to claim 1, wherein mechanically stimulating the bladder comprises controlling a cardiovascular function of the subject selected from the group consisting of: blood pressure, portal pressure, pulmonary pressure, organ blood flow, cardiac output, heart rate, intravascular fluid volume, extravascular fluid volume, pulmonary edema level, and body edema level.

8. The method according to claim 1, wherein mechanically stimulating the subject's bladder comprises inserting a catheter into the bladder, the structure being disposed at a distal end of a catheter, and wherein inserting the catheter comprises facilitating outflow of urine from the bladder via a urine-drainage lumen of the catheter.

9. The method according to claim 1, further comprising detecting a parameter of the subject, wherein mechanically stimulating the bladder comprises mechanically stimulating the bladder responsively to the detected parameter.

10. The method according to claim 9, wherein detecting the parameter comprises detecting impedance of the subject's urine.

11. The method according to claim 9, wherein detecting the parameter comprises detecting a parameter selected from the group consisting of: glomerular filtration rate, urine flow, urine composition, secretion of hormones from the kidney, a creatinine level, and an insulin level.

12. The method according to claim 9, wherein detecting the parameter comprises detecting a parameter selected from the group consisting of: a urinary parameter, urinary peristalsis, and urinary pressure.

13. The method according to claim 9, wherein detecting the parameter comprises detecting a parameter selected from the group consisting of: blood chemistry, blood pressure, heart rate, breathing rate, lung fluid volume, and ECG.

14. The method according to claim 1, wherein mechanically stimulating the bladder with the structure comprises moving the structure with respect to an inner wall of the bladder, while at least a portion of the structure is contacting the inner wall.

15. The method according to claim 14, wherein the structure includes a structure disposed at an end of a transurethral catheter, and wherein moving the structure comprises performing an action selected from the group consisting of: vibrating the catheter, pushing the catheter, pulling the catheter, and modulating a length of the catheter.

16. The method according to claim 14, wherein the structure includes a device that is configured to remain inside the subject's bladder in the absence of a transurethral catheter, and wherein moving the structure comprises moving the device.

17. The method according to claim 14, wherein moving the structure comprises directing energy toward the structure from a location outside a body of the subject.

18. The method according to claim 17, wherein directing energy toward the structure comprises directing a magnetic field toward the structure.

19. The method according to claim 17, wherein directing energy toward the structure comprises directing waves toward the structure, the waves being selected from the group consisting of: sonic waves and ultrasonic waves.

20. The method according to claim 14, wherein the structure includes a balloon, and wherein moving the structure with respect to the inner wall of the bladder comprises moving the balloon with respect to the inner wall of the bladder.

21. The method according to claim 20, wherein the balloon includes protruding members that protrude therefrom, and wherein mechanically stimulating the bladder comprises moving the protruding members with respect to the inner wall of the bladder.

22. The method according to claim 20, wherein moving the balloon with respect to the inner wall of the bladder comprises modulating a volume of the balloon.

23. The method according to claim 22, wherein modulating the volume of the balloon comprises modulating the volume of the balloon at a frequency of 0.1 Hz to 1 Hz.

24. The method according to claim 20, wherein mechanically stimulating the bladder comprises inflating the balloon to a volume of more than 30 cc.

25. The method according to claim 24, wherein mechanically stimulating the bladder comprises inflating the balloon to a volume of more than 50 cc.

26. The method according to claim 25, wherein mechanically stimulating the bladder comprises inflating the balloon to a volume of more than 100 cc.

27. A method, comprising:
   identifying a subject as suffering from an impaired body system, the body system being selected from the group consisting of: a cardiovascular system and a renal system; and
   in response thereto, treating the impaired body system of the subject, by mechanically stimulating a bladder of the subject, by directing toward the subject's bladder waves selected from the group consisting of: sonic waves and ultrasonic waves.

28. A method, comprising:
   identifying a subject as suffering from an impaired body system, the body system being selected from the group consisting of: a cardiovascular system and a renal system;
   in response thereto:
   inserting a structure inside a bladder of the subject; and
   mechanically stimulating the bladder with the structure; and
   detecting a parameter of the subject selected from the group consisting of: blood chemistry, blood pressure, heart rate, breathing rate, lung fluid volume, and ECG, mechanically stimulating the bladder comprising mechanically stimulating the bladder responsively to the detected parameter.

29. A method, comprising:

identifying a subject as suffering from an impaired body system, the body system being selected from the group consisting of: a cardiovascular system and a renal system; and in response thereto:

inserting a balloon inside a bladder of the subject; and mechanically stimulating the bladder with the balloon, by moving the balloon with respect to an inner wall of the bladder, while the balloon is contacting the inner wall of the bladder, by modulating a volume of the balloon.

30. The method according to claim 22, wherein modulating the volume of the balloon comprises modulating the volume of the balloon at a frequency of 0.1 Hz to 1 Hz.

31. A method, comprising:

identifying a subject as suffering from an impaired body system, the body system being selected from the group consisting of: a cardiovascular system and a renal system; and in response thereto:

inserting a balloon inside a bladder of the subject; and mechanically stimulating the bladder with the balloon, by inflating the balloon to a volume of more than 30 cc, and by moving the balloon with respect to an inner wall of the bladder, while the balloon is contacting the inner wall of the bladder.

32. The method according to claim 31, wherein mechanically stimulating the bladder comprises inflating the balloon to a volume of more than 50 cc.

33. The method according to claim 32, wherein mechanically stimulating the bladder comprises inflating the balloon to a volume of more than 100 cc.

* * * * *